United States Patent
Hosoya et al.

(10) Patent No.: US 9,102,987 B2
(45) Date of Patent: Aug. 11, 2015

(54) **METHOD OF DETECTING *PAECILOMYCES VARIOTII***

(75) Inventors: Kouichi Hosoya, Haga-gun (JP);
Motokazu Nakayama, Haga-gun (JP);
Hajime Tokuda, Haga-gun (JP);
Takashi Yaguchi, Chiba (JP); Yusuke Hiro, Chiba (JP)

(73) Assignee: Kao Corporation, Tokyo (JP)

( * ) Notice: Subject to any disclaimer, the term of this patent is extended or adjusted under 35 U.S.C. 154(b) by 429 days.

(21) Appl. No.: 12/994,571

(22) PCT Filed: May 29, 2009

(86) PCT No.: PCT/JP2009/059891
§ 371 (c)(1),
(2), (4) Date: Jan. 7, 2011

(87) PCT Pub. No.: WO2009/145314
PCT Pub. Date: Dec. 3, 2009

(65) Prior Publication Data
US 2011/0104699 A1    May 5, 2011

(30) Foreign Application Priority Data
May 29, 2008 (JP) .................................. 2008-141500

(51) Int. Cl.
*C12Q 1/68* (2006.01)
*C07K 14/37* (2006.01)
*C07H 21/04* (2006.01)

(52) U.S. Cl.
CPC .............. *C12Q 1/6895* (2013.01); *C07K 14/37* (2013.01)

(58) Field of Classification Search
None
See application file for complete search history.

(56) References Cited

U.S. PATENT DOCUMENTS 6,117,636 A    9/2000    Chrzavzez nee Taddei et al.

FOREIGN PATENT DOCUMENTS

| CA | 2 378 407 A1 | 1/2001 |
| JP | 11-505728 | 5/1999 |
| JP | 2006-061152 | 3/2006 |
| JP | 2006-304763 | 11/2006 |
| JP | 2007-174903 | 7/2007 |
| WO | WO 9947706 A1 * | 9/1999 |
| WO | WO 01/04281 A2 | 1/2001 |

OTHER PUBLICATIONS

Samson, R.A. et al. Persoonia 22:14-27 (Feb. 10, 2009).*
Extended European Seach Report for EP Appl. No. 09754822.6, mailed Nov. 14, 2011 from the European Patent Office, Munich, Germany.

(Continued)

*Primary Examiner* — Diana B Johannsen
(74) *Attorney, Agent, or Firm* — Sterne, Kessler, Goldstein & Fox P.L.L.C.

(57) ABSTRACT

A method of detecting *Paecilomyces variotii*, containing identifying *Paecilomyces variotii* using a nucleic acid represented by the following nucleotide sequence (a) or (b):

(a) a partial nucleotide sequence of a β-tubulin gene set forth in any one of SEQ ID NOS: 1 to 4 and 22 to 33, or a complementary sequence thereof; and (b) a nucleotide sequence which includes a nucleotide sequence set forth in any one of SEQ ID NOS: 1 to 4 and 22 to 33 which has a deletion, substitution, or addition of one to several nucleotides and can be used for detecting *Paecilomyces variotii*, or a complementary sequence thereof.

12 Claims, 5 Drawing Sheets

(56) References Cited

OTHER PUBLICATIONS

Houbraken, J et al., "Sexual Reproduction as the Cause of Heat Resistance in the Food Spoilage Fungus *Byssochlamys spectabilis*(Anamorph *Paecilomyces variotii*), " Appl. Envir. Microbiol. 74: 1613-1619 (Mar. 2008) American Soc. Microbiology, Washington, DC.

Glass NL et al., "Development of primer sets designed for use with the PCR to amplify conserved genes from filamentous ascomycetes," Appl. Envir. Microbiol., 61:1323-1330 (Apr. 1995), American Soc. Microbiology, Washington, DC.

Kantarcioglu, AS et al., "*Paecilomyces variotii*central nervous system infection in a patient with cancer," Mycoses 46(1-2): 45-50 (Feb. 2003), Blackwell Publishing Ltd, Oxford, England.

Accession No. AY753362, retrieved from EBI accession No. AY753362, entry created Mar. 30, 2006, updated May 13, 2009, updated May 13, 2009, "*Paecilomyces variotii*strain CBS 102.74 beta-tubulin gene, partial sequence".

Accession No. EU037075, retrieved from EBI accession No. AY75336, entry created Mar. 11, 2008, updated Mar. 11, 2008, *Byssochlamys spectabilis—Talaromyces spectabilis*strain CBS 121587 beta-tubulin gene, partial cds.

Unverified human translation of a report by Aoyama, F., "Identification of Heat resistance Fungi in fruit juice based on DNA sequence analysis," Kajitsu Kyohaiho, Association of Fruit Juice, Report No. 569, pp. 4-15, Japan Fruit Juice Association, Tokyo, Japan (Jan. 2006) [previously cited as document NPL4].

Translation of International Search Report for PCT/JP2009/059891; I.A. fd: May 29, 2009, mailed Jun. 23, 2009 from the Japanese Patent Office, Tokyo, Japan.

International Preliminary Report on Patentability, Chapter I of the Patent Cooperation Treaty, including a translation of the Written Opinion for PCT/JP2009/059891; I.A. fd: May 29, 2009, issued Jan. 11, 2011 from the International Bureau of WIPO, Geneva, Switzerland.

NCBI Sequence Accession No. AY753365 version AY753365.1, *Paecilomyces variotii*strain CBS 628.66 beta-tubulin gene, partial sequence, Mar. 30, 2006, National Center for Biotechnology Information, Bethesda, MD.

Aoyama, F., "Identification of Heat resistance fungi in fruit juice based on DNA sequence analysis," ("Kajitsu Inryochu ni Okeru Tainetsusei Kabi no DNA Dotei"), Assoc. of Fruit Juice (Kaju Kyokaiho) Report No. 569: 4-15 (Jan. 2, 2006), Association of Fruit Juice, Tokyo, Japan.

Donaldson, GC et al., "Primer Sets Developed to Amplify Conserved Genes from Filamentous Ascomycetes Are Useful in Differentiating Fusarium Species Associated with Conifers," Appl. Envir. Microbiol. 61:1331-1340 (Apr. 1995), American Soc. Microbiology, Washington, DC.

Houbraken, J et al., "Sexual Reproduction as the Cause of Heat Resistance in the Food Spoilage Fungus *Byssochlamys spectabilis*(Anamorph *Paecilomyces variotii*)," Appl. Envir. Microbiol. 74:1613-1619, (Mar. 2008), American Soc. Microbiology, Washington, DC.

Kalkar, O, et al., "Characterization of an Indonesian isolate of *Paecilomyces reniformis*," Mycopathologia 161(2):109-118 (Feb. 2006), Springer, Netherlands.

Luangsa-Ard, JJ et al., "On the relationships of *Paecilomyces*sect. *Isarioidea*species," Mycol Res 109(Pt 5): 581-589 (May 2005), The British Mycological Society, Cambridge, England.

Tubu, D et al., "Mycological identification of pulmonary infection of calves with mimetic Penicillium, " Chienese J Veterinary Medicine vol. 22: issue 12, pp. 17-18 (Dec. 1996), China Animal Husbandry and Veterinary Institute, Beijing, China.

Extended European search report including the European search report and the European search opinion, for EP Application No. 14161498.2, dated Jul. 11, 2014, European Patent Office, Munich, Germany.

Nakayama, M et al., "A rapid method for identifying *Byssochlamys*and *Hamigera*," J Food Prot, Aug. 2010; 73(8): 1486-1492, International Assoc for Food Protection, Des Moine, IA.

\* cited by examiner

FIG. 1

Partial nucleotide sequence of β-tubulin gene of *Paecilomyces variotii* IFM40913 strain, and position recognized by the primers of primer set 1 of the present invention

```
  1  TGGTAACCAA ATCGGTGCTG CTTTCTGGTA TGTTGTCAAC CAGCAGGAGA AATGAAACAA AGAGCCTAGA GTCCGTTTGG   80
     ********** ********** ********** ********** ********** ********** ********** **********

< ========F3 ========>                      <====
 81  GGACGTGGAA GGCTCAAGTG ATCAGAATTG GAGGTGCTAA CGATCCTATA GGCAGACCAT CTCTGGTGAG CACGGCCTTG  160
     ********** ********** ********** ********** ********** ********** ********** **********

===F2===== ==>
161  ACGGCTCTGG TGTGTAAGTA CACGATATCT GGGGATGCTT CGACACGGAA TCGAGAGAGA CGACTGACGA TGGATTAGCT  240
     ********** ********** ********** ********** ********** ********** ********** **********
                    <===== ===LF===== ====>     <========= F1c======= =>
                    <=======B1c=======>         <======= =LB======= ==>

241  ACAATGGCTC CTCCGACCTT CAGCTCGAGC GCATGAACGT CTACTTCAAC GAGGTAGTTG TTGACCCTAT GATCCCAAGA  320
     ********** ********** ********** ********** ********** ********** ********** **********
                                                                                   <=======B

321  GGAACGCTCC ATGAGCTCAC CAATAAATAG GCCGCTGGCA AGAAGTACGT TCCTCGTGCC GTCCTCGTCG ACCTCGAGCC  400
     ********** ********** ********** ********** ********** ********** ********** **********
     2========>         <= =======B3= =======>

401  TGGTACCATG GACGCTGTCC GTGCTGGTCC TTTCGGCCAG CTCTTCCGCC CTGACAACTT CGTCTTCGGT CAGTCCGGTG  480
     ********** ********** ********** ********** ********** ********** ********** **********

481  CTGGTAACAA CTGGGCCAAG GGTCACTACA CTG                                                     513
     ********** ********** ********** ***
```

\* represents a nucleotide in the complementary strand.

FIG. 2

Partial nucleotide sequence of β-tubulin gene of each of
Paecilomyces variotii IFM40913 and IFM40915 strains, and position
recognized by the primers of primer set 2 of the present invention

```
P_variotii_40913   AGACCCTAGAGTCCGTTTGGGGACGTGCAAGGCTCAAGTGATCAGAATTGGAGGTCCTAA 120
P_variotii_40915   AGACCCTGGAGTCCGTTTGGGGACGTCCAAGGCTCAAGTGATGAGACTTGGAGGTCCTAA 120
                   ************************************************************

P_variotii_40913   CGATCCTATAGGCAGACCATCTCTGGTGAGCACGGCCTTGACGGCTCTGGTGTGTAAGTA 180
P_variotii_40915   CGACCCTATAGGCAGACCATCTCTGGTGAGCACGGCCTTGACGGCTCCGGTGTGTAAGTA 180
                   ************************************************************

<========F3========>      <========F2=========>
P_variotii_40913   CACGATATCTGGGCATGCTTCGACACGGAATCGAGAGAGACGACTGACGATGGATTAGCT 240
P_variotii_40915   CACGATATCTGGGGATGCTTCGACACGGAATCGAGAGAGACGACTGACGATGGATTAGCT 240
                   ***********************************************************
                                                                        <=====

P_variotii_40913   ACAATGGCTCCTCCGACC---TTCAGCTCGAGCGCATGAACGTCTACTTCAACGAGGTAG 297
P_variotii_40915   ACAATGGCTCCTCCGACNACCTTCAGCTCGAGCGCATGAATGTCTACTTCAACGAGGTAG 300
                   *****************   *********************** ***************
                   ===LF========> <=========Flc=========>
                                      <========B1c=========>     <========LB=========>
P_variotii_40913   TTGTTGACCCTATGATCCCAAGAGGAACGCTCCATGAGCTCACCAATAAATAGGCCGCTG 357
P_variotii_40915   TTGTTGACCCTATGATCCCAAGAGGAACGCCCCATGAGCTCACCAATAAATAGGCCGCTG 360
                   *************************************************************
                                                                             <

P_variotii_40913   GCAAGAAGTACGTTCCTCGTGCCGTCCTCGTCGACCTCGAGCCTGGTACCATGGACGCTG 417
P_variotii_40915   GCAAGAAGTACGTTCCTCGTGCCGTCCTCGTCGACCTCGAGCCTGGTACCATGGACGCTG 420
                   ************************************************************
                   ===B2=============>                        <========B3=======>
```

\* represents a nucleotide in the complementary strand.

FIG. 3

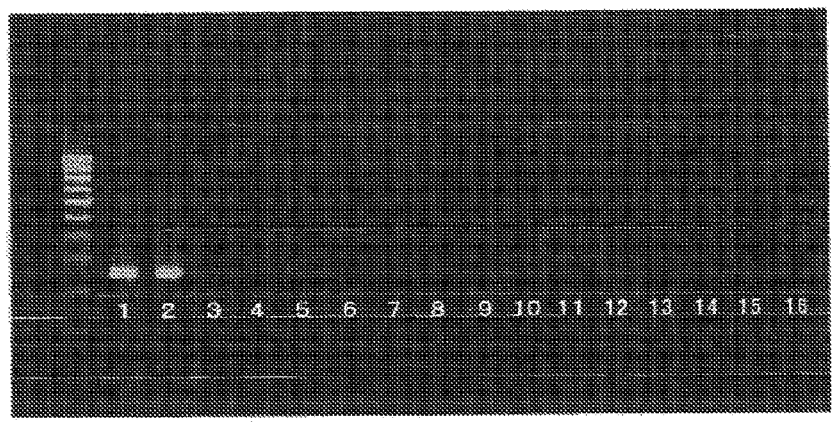

_US 9,102,987 B2_

METHOD OF DETECTING *PAECILOMYCES VARIOTII*

REFERENCE TO SEQUENCE LISTING SUBMITTED ELECTRONICALLY

The content of the electronically submitted substitute sequence listing, file name: 2537_0430000_sequencelisting_2ndSubstitute_ascii.txt, size: 17,083 bytes; and date of creation Jan. 20, 2015, filed herewith, is incorporated herein by reference in its entirety.

TECHNICAL FIELD

The present invention relates to a method of detecting *Paecilomyces Variotii*.

BACKGROUND ART

*Paecilomyces variotii* is an imperfect fungus which is widely distributed throughout nature. *Paecilomyces variotii* forms asexual spores including double cell walls called chlamydospores in its life cycle. The chlamydospores of *Paecilomyces variotii* are known to have very high resistance to stress, and to live and proliferate even under conditions for sterilizing general fungi by heat and a reagent, resulting in growth of mold. Therefore, *Paecilomyces variotii* is regarded as a harmful fungus in food industry and toiletry industry. Accordingly, in establishment of antiseptic and antifungal systems, detection and identification of *Paecilomyces variotii* is considered to be very important.

Detection and identification of *Paecilomyces variotii* is performed mainly by morphological classification through culture. In this method, it is necessary to continue the culture until morphological characters appear, and hence it takes a long period of time (at least 14 days) to perform the method. Moreover, the morphological identification requires a very high level of professionalism, and the identification results may vary depending on judges and have a problem in reliability. Therefore, it is required to establish a detection and identification method which solves the problems of rapidness and reliability.

As a method of rapidly and reliably detecting a fungus, an amplification method which targets a specific nucleotide sequence of a gene (such as the PCR method or the LAMP method) is known (see, for example, JP-T-11-505728 ("JP-T" means searched and published International patent publication), JP-A-2006-61152 ("JP-A" means unexamined published Japanese patent application), JP-A-2006-304763 and JP-A-2007-174903). However, a gene region specific to *Paecilomyces variotii* has not been clarified. Therefore, such method has a problem in that it is difficult to detect *Paecilomyces variotii* specifically and rapidly.

SUMMARY OF INVENTION

An object of the present invention is to provide a method with which *Paecilomyces variotii* can be detected specifically, easily, and rapidly, which is known to be a harmful fungus in food industry and toiletry industry. A further object of the present invention is to provide DNA, a primer set, an oligonucleotide and a detection kit, which can be applied to the method.

The difficulty in detection of *Paecilomyces variotii* as described above is caused by false positive and false negative results in the PCR method using known conventional primers. The inventors of the present invention considered that this problem is caused by difficulty in design of sensitive primers for specifically and rapidly detecting and discriminating *Paecilomyces variotii* because database of the genes of *Paecilomyces variotii* is now weak and the gene region specific to *Paecilomyces variotii*, conserved at species level, has not been clarified accurately.

In view of such problems, the inventors of the present invention have made extensive studies to search a novel DNA region capable of specifically detecting and discriminating *Paecilomyces variotii*. As a result, the inventors have found out that the β-tubulin gene of *Paecilomyces variotii* includes a region having a specific nucleotide sequence which can be clearly different from that of another fungus (hereinafter, also referred to as "variable region"). Moreover, the inventors have found out that such *Paecilomyces variotii* can be detected specifically and rapidly by targeting the variable region. The present invention has been completed based on the findings.

The present invention resides in a method of detecting *Paecilomyces variotii*, containing identifying *Paecilomyces variotii* using a nucleic acid represented by the following nucleotide sequence (a) or (b):

(a) a partial nucleotide sequence of a β-tubulin gene set forth in any one of SEQ ID NOS: 1 to 4 and 22 to 33, or a complementary sequence thereof; and (b) a nucleotide sequence which includes a nucleotide sequence set forth in any one of SEQ ID NOS: 1 to 4 and 22 to 33 which has a deletion, substitution, or addition of one to several nucleotides and can be used for detecting *Paecilomyces variotii*, or a complementary sequence thereof.

Further, the present invention resides in a DNA represented by the nucleotide sequence (a) or (b) described above which is used for detecting *Paecilomyces variotii*.

Further, the present invention resides in an oligonucleotide for detecting *Paecilomyces variotii*, which can hybridize with a nucleic acid represented by the nucleotide sequence (a) or (b) described above and act as a nucleic acid probe or nucleic acid primer for specifically detecting *Paecilomyces variotii*.

Further, the present invention resides in an oligonucleotide pair or oligonucleotide group for detecting *Paecilomyces variotii*, containing at least one pair or one group selected from the group consisting of a pair of the following oligonucleotides (c) and (d), a pair of the following oligonucleotides (e) and (f), a pair of the following oligonucleotides (e) and (g), and a group of the following oligonucleotides (e), (f), and (g):

(c) an oligonucleotide represented by the nucleotide sequence set forth in SEQ ID NO: 5, or an oligonucleotide represented by a nucleotide sequence which has 70% or more homology to the nucleotide sequence set forth in SEQ ID NO: 5 and can be used as a nucleic acid primer;

(d) an oligonucleotide represented by the nucleotide sequence set forth in SEQ ID NO: 6, or an oligonucleotide represented by a nucleotide sequence which has 70% or more homology to the nucleotide sequence set forth in SEQ ID NO: 6 and can be used as a nucleic acid primer;

(e) an oligonucleotide represented by the nucleotide sequence set forth in SEQ ID NO: 7, or an oligonucleotide represented by a nucleotide sequence which has 70% or more homology to the nucleotide sequence set forth in SEQ ID NO: 7 and can be used as a nucleic acid primer;

(f) an oligonucleotide represented by the nucleotide sequence set forth in SEQ ID NO: 8, or an oligonucleotide represented by a nucleotide sequence which has 70% or more homology to the nucleotide sequence set forth in SEQ ID NO: 8 and can be used as a nucleic acid primer; and (g) an oligonucleotide represented by the nucleotide sequence set forth in SEQ ID NO: 9, or an oligonucleotide represented by a nucleotide sequence which has 70% or more homology to the nucleotide sequence set forth in SEQ ID NO: 9 and can be used as a nucleic acid primer.

Further, the present invention relates to a kit for detecting *Paecilomyces variotii*, containing the above-described oligonucleotide pair or oligonucleotide group.

Further, the present invention relates to a primer set, containing:
a primer consisting of the nucleotide sequence set forth in SEQ ID NO: 10;
a primer consisting of the nucleotide sequence set forth in SEQ ID NO: 11;
a primer consisting of the nucleotide sequence set forth in SEQ ID NO: 12;
a primer consisting of the nucleotide sequence set forth in SEQ ID NO: 13;
a primer consisting of the nucleotide sequence set forth in SEQ ID NO: 14; and
a primer consisting of the nucleotide sequence set forth in SEQ ID NO: 15;
wherein the primer set is used for detecting *Paecilomyces variotii* by Loop mediated isothermal amplification (LAMP) method.

Further, the present invention relates to a primer set, containing:
a primer consisting of the nucleotide sequence set forth in SEQ ID NO: 10;
a primer consisting of the nucleotide sequence set forth in SEQ ID NO: 11;
a primer consisting of the nucleotide sequence set forth in SEQ ID NO: 12; and
a primer consisting of the nucleotide sequence set forth in SEQ ID NO: 13;
wherein the primer set is used for detecting *Paecilomyces variotii* by Loop mediated isothermal amplification (LAMP) method.

Further, the present invention relates to a primer set, containing:
a primer consisting of the nucleotide sequence set forth in SEQ ID NO: 16;
a primer consisting of the nucleotide sequence set forth in SEQ ID NO: 17;
a primer consisting of the nucleotide sequence set forth in SEQ ID NO: 18;
a primer consisting of the nucleotide sequence set forth in SEQ ID NO: 19;
a primer consisting of the nucleotide sequence set forth in SEQ ID NO: 20; and
a primer consisting of the nucleotide sequence set forth in SEQ ID NO: 21;
wherein the primer set is used for detecting *Paecilomyces variotii* by Loop mediated isothermal amplification (LAMP) method.

Further, the present invention relates to a primer set, containing:
a primer consisting of the nucleotide sequence set forth in SEQ ID NO: 16;
a primer consisting of the nucleotide sequence set forth in SEQ ID NO: 17;
a primer consisting of the nucleotide sequence set forth in SEQ ID NO: 18; and
a primer consisting of the nucleotide sequence set forth in SEQ ID NO: 19;
wherein the primer set is used for detecting *Paecilomyces variotii* by Loop mediated isothermal amplification (LAMP) method.

Further, the present invention relates to a kit for detecting Paecilomyces variotii, containing:
the above-described primer set for use in the LAMP method;
a DNA polymerase; and
dNTP containing dATP, dCTP, dGTP and dTTP.

According to the present invention, it is possible to provide a method with which *Paecilomyces variotii* can be detected specifically, easily, and rapidly, which is known to be a harmful fungus in food industry and toiletry industry. Further, according to the present invention, it is possible to provide DNA, a primer set, an oligonucleotide and a detection kit, which can be applied to the method.

BRIEF DESCRIPTION OF DRAWINGS

[FIG. 1] FIG. 1 is a diagram illustrating the position relationship of nucleotide sequences recognized by the primers of primer set 1 of the present invention in the nucleotide sequence of the β-tubulin gene of *Paecilomyces variotii* IFM40913 strain SEQ ID NO:1.

[FIG. 2] FIG. 2 is a diagram illustrating the position relationship of nucleotide sequences recognized by the primers of primer set 2 of the present invention in the nucleotide sequence of the β-tubulin genes of *Paecilomyces variotii* IFM40913 strain and (bases 61-417 of SEQ ID NO: 1) and *Paecilomyces variotii* IFM40915 strain (bases 61-420 of SEQ ID NO: 2).

[FIG. 3] FIG. 3 is an electrophoretogram of PCR products obtained by using the oligonucleotides (c) and (d) of the present invention in Example 1.

FIG. 4 is an electrophoretogram of PCR products obtained by using the oligonucleotides (c) and (d) of the present invention in Example 1.

FIG. 5 is a graph illustrating the detection sensitivity of *Paecilomyces variotii* by real-time turbidity monitoring method in Example 2. The numeral 1 denotes the detection sensitivity of a sample including genomic DNA derived from *Paecilomyces variotii* IFM40913 strain; the numeral 2 denotes the detection sensitivity of a sample including genomic DNA derived from *Paecilomyces variotii* IFM40915 strain; the numeral 4 denotes the detection sensitivity of a sample including genomic DNA derived from *Byssochlamys nivea* IFM51244 strain; the numeral 5 denotes the detection sensitivity of a sample including genomic DNA derived from *Hamigera avellanea* IFM42323 strain; and the numeral 7 denotes the detection sensitivity of a sample including genomic DNA derived from *Talaromyces luteus* IFM53242 strain.

In FIG. 6(*a*), the numeral 1 denotes the detection sensitivity of a sample including genomic DNA derived from *Paecilomyces variotii* IFM40913 strain; the numeral 2 denotes the detection sensitivity of a sample including genomic DNA derived from *Paecilomyces variotii* IFM40915 strain; the numeral 3 denotes the detection sensitivity of a sample including genomic DNA derived from *Byssochlamys fluva* IFM48421 strain; the numeral 7 denotes the detection sensitivity of a sample including genomic DNA derived from *Neosartorya ficheri* IFM46945 strain; and the numeral 8 denotes the detection sensitivity of a sample including genomic DNA derived from *Neosartotya spinosa* IFM46967 strain. In FIG. 6(*b*), the numeral 9 denotes the detection sensitivity of a sample including genomic DNA derived from *Neosartorya glabra* IFM46949 strain; the numeral 10 denotes the detection sensitivity of a sample including genomic DNA derived from *Neosartorya hiratsukae* IFM47036 strain; the numeral 11 denotes the detection sensitivity of a sample including genomic DNA derived from *Alterraria alternate* IFM41348 strain; the numeral 12 denotes the detection sensitivity of a sample including genomic DNA derived from *Aureobasidium pullulans* IFM41409 strain; the numeral 14 denotes the detection sensitivity of a sample including genomic DNA derived from *Fusarium oxysporum* IFM50002 strain; and the numeral 15 denotes the detection sensitivity of a sample including genomic DNA derived from *Trichoderma viride* IFM40938 strain.

FIG. 7 is an electrophoretogram of PCR products obtained by using the oligonucleotides (e) to (g) of the present invention in Example 4.

MODE FOR CARRYING OUT THE INVENTION

Figure 4:
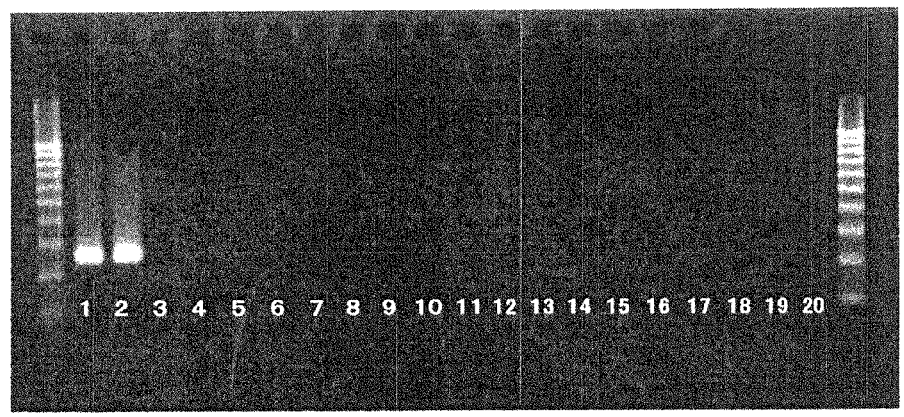
[FIG. 4]

Hereinafter, the present invention is described in detail.

The present invention is a method of specifically discriminating and detecting *Paecilomyces variotii* by identifying *Paecilomyces variotii* using a nucleic acid represented by a specific partial nucleotide sequence of the β-tubulin gene of *Paecilomyces variotii*, i.e., a nucleic acid represented by a nucleotide sequence in a region (variable region) which is present in the β-tubulin gene sequence of *Paecilomyces variotii* and is specific to *Paecilomyces variotii*. In this description, the "variable region" is a region where nucleotide mutations tend to accumulate in the β-tubulin gene, and the nucleotide sequence in this region is significantly different from that of another fungus. The "*Paecilomyces variotii*" in the present invention is a filamentous deuteromycete and belongs to the genus *Paecilomyces*. Further, the "β-tubulin" is a protein which constitutes a microtubule, and the "β-tubulin gene" is a gene encoding β-tubulin.

In the method of detecting *Paecilomyces variotii* of the present invention, *Paecilomyces variotii* is identified using a nucleic acid represented by the following nucleotide sequence (a) or (b).
(a) A partial nucleotide sequence of a β-tubulin gene set forth in any one of SEQ ID NOS: 1 to 4 and 22 to 33, or a complementary sequence thereof
(b) A nucleotide sequence which includes a nucleotide sequence set forth in any one of SEQ ID NOS: 1 to 4 and 22 to 33 which has a deletion, substitution, or addition of one to several nucleotides and can be used for detecting *Paecilomyces variotii*, or a complementary sequence thereof.

The variable region of the β-tubulin gene represented by the nucleotide sequence (a) or (b) has a nucleotide sequence specific to *Paecilomyces variotii* and can be clearly different from that of another general fungus. Therefore, according to the method of detecting *Paecilomyces variotii* of the present invention, *Paecilomyces variotii* can be detected specifically and rapidly. Moreover. DNA represented by the nucleotide sequence (a) or (b) can be used for detecting *Paecilomyces variotii*.

Partial nucleotide sequences of the β-tubulin gene of *Paecilomyces variotii* are described based on SEQ ID NOS: 1 and 2. The nucleotide sequence set forth in SEQ ID NO: 1 is a partial nucleotide sequence of the β-tubulin gene of *Paecilomyces variotii* IFM40913 strain, and the nucleotide sequence set forth in SEQ ID NO: 2 is a partial nucleotide sequence of the β-tubulin gene of *Paecilomyces variotii* IFM40915 strain.

Moreover, parts of the partial nucleotide sequences of the β-tubulin gene of *Paecilomyces variotii* IFM40913 and IFM40915 strain set forth in SEQ ID NOS: 1 and 2 are compared and described in FIG. 2. The inventors of the present invention have found out that the nucleotide sequences in the region of the position 50 to 100 and the region of the position 280 to 340 in the nucleotide sequences set forth in SEQ ID NOS: 1 and 2 are particularly poorly conserved among the fungi, and each of the fungi species has a specific nucleotide sequence in these regions. The present invention targets these partial nucleotide sequences of the β-tubulin gene.

Moreover, partial nucleotide sequences of the β-tubulin gene of *Paecilomyces variotii* are described based on SEQ ID NOS: 3 and 4 and 22 to 33.

The nucleotide sequence set forth in SEQ ID NO: 3 represents a partial nucleotide sequence of the β-tubulin gene of *Paecilomyces variotii* EUO37073 strain.

The nucleotide sequence set forth in SEQ ID NO: 4 represents a partial nucleotide sequence of the β-tubulin gene of *Paecilomyces variotii* IFM50293 strain.

The nucleotide sequence set forth in SEQ ID NO: 22 represents a partial nucleotide sequence of the β-tubulin gene of *Paecilomyces variotii* NBRC4855 strain.

The nucleotide sequence set forth in SEQ ID NO: 23 represents a partial nucleotide sequence of the β-tubulin gene of *Paecilomyces variotii* IFM52147 strain.

The nucleotide sequence set forth in SEQ ID NO: 24 represents a partial nucleotide sequence of the β-tubulin gene of *Paecilomyces variotii* IFM52145 strain.

The nucleotide sequence set forth in SEQ ID NO: 25 represents a partial nucleotide sequence of the β-tubulin gene of *Paecilomyces variotii* IFM51028 strain.

The nucleotide sequence set forth in SEQ ID NO: 26 represents a partial nucleotide sequence of the β-tubulin gene of *Paecilomyces variotii* IFM51195 strain.

The nucleotide sequence set forth in SEQ ID NO: 27 represents a partial nucleotide sequence of the β-tubulin gene of *Paecilomyces variotii* IFM55619 strain.

The nucleotide sequence set forth in SEQ ID NO: 28 represents a partial nucleotide sequence of the β-tubulin gene of *Paecilomyces variotii* NBRC5479 strain.

The nucleotide sequence set forth in SEQ ID NO: 29 represents a partial nucleotide sequence of the β-tubulin gene of *Paecilomyces variotii* IFM51027 strain.

The nucleotide sequence set forth in SEQ ID NO: 30 represents a partial nucleotide sequence of the β-tubulin gene of *Paecilomyces variotii* NBRC31967 strain.

The nucleotide sequence set forth in SEQ ID NO: 31 represents a partial nucleotide sequence of the β-tubulin gene of *Paecilomyces variotii* NBRC31685 strain.

The nucleotide sequence set forth in SEQ ID NO: 32 represents a partial nucleotide sequence of the β-tubulin gene of *Paecilomyces variotii* SUM3339 strain.

The nucleotide sequence set forth in SEQ ID NO: 33 represents a partial nucleotide sequence of the β-tubulin gene of *Paecilomyces variotii* IFM50294 strain.

The inventors of the present invention have found out that the partial nucleotide sequences of the β-tubulin gene are also particularly poorly conserved among the fungi, and each of the fungi species has a specific nucleotide sequence. The present invention also targets the partial nucleotide sequences of the β-tubulin gene.

The nucleic acid represented by the partial nucleotide sequence of the β-tubulin gene of *Paecilomyces variotii* to be used in the detection method of the present invention (the nucleotide sequence in the variable region) is a nucleic acid represented by the nucleotide sequence set forth in any one of SEQ ID NOS: 1 to 4 and 22 to 33 or the complementary sequence thereof.

The nucleotide sequences set forth in SEQ ID NOS: 1 to 4 and 22 to 33 or complementary sequences thereof are nucleotide sequences of the variable regions of the β-tubulin gene, which are isolated and identified from *Paecilomyces variotii* IFM40913, IFM40915, EUO37073, IFM50293, NBRC4855, IFM52147, IFM52145, IFM51028, IFM51195, IFM55619, NBRC5479, IFM51027, NBRC31967, NBRC31685, SUM3339 and IFM50294, respectively. These sequences have very high homology in *Paecilomyces variotii* and have low homology to a fungus other than *Paecilomyces variotii*, and hence it is possible to specifically distinguish and identify only *Paecilomyces variotii* by confirming whether a sample has such nucleotide sequence or not.

Also in the case of using nucleic acids represented by the nucleotide sequences set forth in SEQ ID NOS: 1 to 4 and 22 to 33 with a deletion, substitution, or addition of one to several nucleotides or complementary sequences thereof, it is possible to specifically distinguish and identify only *Paecilomyces variotii*.

(Hereinafter, the nucleotide sequence set forth in any one of SEQ ID NOS: 1 to 4 and 22 to 33 or a complementary sequence thereof, and the nucleotide sequence set forth in any one of SEQ ID NOS: 1 to 4 and 22 to 33 with a deletion, substitution, or addition of one to several nucleotides, which can be used for detecting *Paecilomyces variotii*, or a complementary sequence thereof are also referred to as "nucleotide sequences in variable regions of the β-tubulin gene of the present invention".)

The method of identifying *Paecilomyces variotii* using a nucleic acid represented by the nucleotide sequence in the variable region of the β-tubulin gene of the present invention is not particularly limited, and may be performed by a usual genetic engineering procedure such as a sequencing method, a hybridization method, a PCR method, or a LAMP method.

In the detection method of the present invention, in order to identify *Paecilomyces variotii* using the nucleic acid represented by the nucleotide sequence in the variable region of the β-tubulin gene of the present invention, the nucleotide sequence of the β-tubulin gene in a sample is preferably determined to confirm whether the nucleotide sequence in the gene includes the nucleotide sequence of the nucleic acid (a) or (b) or not. That is, the detection method of the present invention includes: analyzing and determining the nucleotide sequence of the β-tubulin gene in a sample; comparing the determined nucleotide sequence with the nucleotide sequence in the variable region of the β-tubulin gene of the present invention; and identifying *Paecilomyces variotii* based on the matching or difference.

The method of analyzing and determining the nucleotide sequence is not particularly limited, and usual RNA or DNA sequencing means may be used.

Specific examples of the method include an electrophoresis method such as a Maxam-Gilbert method or a Sanger method, mass spectrometry, and a hybridization method. Examples of the Sanger method include a method of labeling a primer or terminator by a radiation labeling method, a fluorescent labeling method, or the like.

In the present invention, in order to identify and detect *Paecilomyces variotii* using the nucleic acid represented by the nucleotide sequence in the variable region of the β-tubulin gene of the present invention, an oligonucleotide for detection which can hybridize with the nucleic acid represented by the nucleotide sequence in the variable region of the β-tubulin gene of the present invention and acts as a nucleic acid probe or a nucleic acid primer may be used.

The oligonucleotide for detection of the present invention may be one which can be used for detecting *Paecilomyces variotii*. That is, the oligonucleotide may be one which can be used as a nucleic acid primer or a nucleic acid probe for detection of *Paecilomyces variotii*, or one which can hybridize with the β-tubulin gene of *Paecilomyces variotii* under stringent conditions. It should be note that, in this description, the "stringent conditions" includes, for example, the method described in Molecular Cloning-A LABORATORY MANUAL THIRD EDITION [Joseph Sambrook, David W. Russell. Cold Spring Harbor Laboratory Press], and examples thereof include conditions where hybridization is performed by incubating a solution containing 6×SSC (composition of 1×SSC: 0.15M sodium chloride, 0.015M sodium citrate, pH7.0), 0.5% SDS, 5×Denhardt and 100 mg/mL herring sperm DNA together with a probe at 65° C. for 8 to 16 hours.

The oligonucleotide for detection of the present invention is more preferably an oligonucleotide represented by the nucleotide sequence which is in a region in the nucleic acid represented by the nucleotide sequence (a) or (b) and is set forth in any one of SEQ ID NOS: 5 to 21, or a complementary sequence thereof. Further, the oligonucleotide for detection of the present invention may be an oligonucleotide represented by a nucleotide sequence which has 70% or more homology to the nucleotide sequence set forth in any one of SEQ ID NOS: 5 to 21 or a complementary sequence thereof, and the homology is more preferably 80% or more, still more preferably 85% or more, even more preferably 90% or more, particularly preferably 95% or more. Further, the oligonucleotide for detection which can be used in the present invention includes an oligonucleotide represented by a nucleotide sequence set forth in any one of SEQ ID NOS: 5 to 21 or a complementary sequence with a mutation or modification such as a deletion, insertion or substitution of one or several, preferably one to five, more preferably one to four, still more preferably one to three, even more preferably one to two, particularly preferably one nucleotide. Moreover, an appropriate nucleotide sequence may be added to the nucleotide sequence set forth in any one of SEQ ID NOS: 5 to 21 or a complementary sequence thereof.

The nucleotide sequence homology is calculated, for example, by Lipman-Pearson method (Science, 227, 1435, (1985)). Specifically, it can be calculated by performing analysis using a homology analysis (Search homology) program of genetic information processing software Genetyx-Win (Software Development) while the unit size to compare (ktup) parameter is set to 2.

The bonding pattern of the oligonucleotide for detection includes not only a phosphodiester bond present in a natural nucleic acid but also a phosphoroamidate bond and a phosphorothioate bond, for example.

The oligonucleotide for detection of the present invention may be used as a nucleic acid primer and a nucleic acid probe. The nucleic acid probe can be prepared by labeling the above-mentioned oligonucleotide with a labeling substance. The labeling substance is not particularly limited and may be a usual labeling substance such as a radioactive substance, an enzyme, a fluorescent substance, a luminescent substance, an antigen, a hapten, an enzyme substrate, or an insoluble carrier. The oligonucleotide may be labeled at its terminal or at the sequence other than the terminals, or at the sugar, phosphate group, or base moiety. Examples of means for detecting the label include: autoradiography in the case of a nucleic acid probe labeled with a radioisotope; a fluorescent microscope in the case of a nucleic acid probe labeled with a fluorescent substance; and an analysis using a sensitive film or a digital analysis using a CCD camera in the case of a nucleic acid probe labeled with a chemiluminescent substance.

Further, the oligonucleotide may be bound to a solid-phase carrier and used as a capture probe. In this case, the capture probe and labeled nucleic acid probe may be combined and used in a sandwich assay, or a target nucleic acid may be labeled and captured.

In the detection method of the present invention, in order to identify and detect *Paecilomyces variotii*, hybridization is performed using, as a nucleic acid probe, preferably an oligonucleotide represented by the nucleotide sequence set forth in any one of SEQ ID NOS: 5 to 21 or the complementary sequence thereof, or an oligonucleotide which has 70% or more homology to the nucleotide sequence set forth in any one of SEQ ID NOS: 5 to 21 or the complementary sequence thereof and can be used as an oligonucleotide for detection, more preferably the oligonucleotide represented by the nucleotide sequence set forth in any one of SEQ ID NOS: 5 to 21.

In order to detect *Paecilomyces variotii* in a sample, an oligonucleotide represented by the nucleotide sequence set forth in any one of SEQ ID NOS: 5 to 21 or the complementary sequence thereof, or an oligonucleotide which has 70% or more homology to the nucleotide sequence set forth in any one of SEQ ID NOS: 5 to 21 or the complementary sequence thereof and can be used as an oligonucleotide for detection is labeled to prepare a nucleic acid probe, and the resultant nucleic acid probe is hybridized with DNA or RNA, followed by detection of the label of the hybridized probe by an appropriate detection method. The nucleic acid probe is hybridized specifically with part of the variable region of the β-tubulin gene of *Paecilomyces variotii*, and hence *Paecilomyces variotii* in a sample can be detected rapidly and easily. As a method of measuring the label of the nucleic acid probe hybridized with DNA or RNA, a usual method (such as a FISH method, a dot-blot method, a Southern-blot method, or a Northern-blot method) may be used.

Further, in the detection method of the present invention, in order to identify *Paecilomyces variotii* using the nucleic acid represented by the nucleotide sequence in the variable region of the β-tubulin gene of the present invention, a DNA fragment including the whole or a partial region of the nucleotide sequence is preferably amplified to confirm whether the amplified product is present or not. The method of amplifying the DNA fragment including the region is not particularly limited, and a usual method such as PCR (polymerase chain reaction) method, LCR (ligase chain reaction) method, SDA (strand displacement amplification) method, NASBA (nucleic acid sequence-based amplification) method, RCA (rolling-circle amplification) method, or LAMP (loop mediated isothermal amplification) method may be used. However, in the present invention, the PCR method or the LAMP method is preferably used.

A case where *Paecilomyces variotii* is detected by performing an amplification reaction by the PCR method in the present invention is described.

A primer consisting of the oligonucleotide for detection of the present invention is preferably an oligonucleotide which can hybridize with a region which is selected from the nucleotide sequence in the variable region of the β-tubulin gene of the present invention and satisfies the following four conditions:

(1) the region contains a nucleotide sequence including about 10 continuous nucleotides in the nucleotide sequence of the gene specific to *Paecilomyces variotii*;

(2) the oligonucleotide has a GC content of about 30% to 80%;

(3) the oligonucleotide has low possibility to cause self-annealing; and (4) the oligonucleotide has a melting temperature (Tm value) of about 55° C. to 65° C.

In the (1) above, the "region contains a nucleotide sequence including about 10 continuous nucleotides in the nucleotide sequence of the gene specific to *Paecilomyces variotii* is present" refers to a region where the nucleotide sequences of different fungi species are particularly poorly conserved (that is, the region has particularly high specificity to *Paecilomyces variotii*) in the variable region of the β-tubulin gene of the present invention and where a nucleotide sequence including about 10 continuous nucleotides in the nucleotide sequence specific to *Paecilomyces variotii* is present. Moreover, in the (3) above, the "oligonucleotide has low possibility to cause self-annealing" means that the primers are expected not to bind to each other due to the nucleotide sequences of the primers.

The number of nucleotides in the oligonucleotide for detection of the present invention is not particularly limited, and is preferably 13 to 30, more preferably 18 to 23. The Tm value of the oligonucleotide in hybridization is preferably in a range of 55° C. to 65° C., more preferably 59° C. to 62° C. The GC content in the oligonucleotide is preferably 30% to 80%, more preferably 45% to 65%, most preferably about 55%.

Further, in the case of identification of *Paecilomyces variotii* using a nucleic acid represented by a partial nucleotide sequence of the β-tubulin gene set forth in SEQ ID NO: 1 or 2 or a complementary sequence thereof, or a nucleic acid represented by the nucleotide sequence which has a deletion, substitution, or addition of one or several nucleotides and can be used for detecting *Paecilomyces variotii*, or a complementary sequence thereof, the whole or part of the nucleotide sequence which is a part of the nucleotide sequences set forth in SEQ ID NOS: 1 and 2 and is located at the position 50 to 100 and/or the position 280 to 340 of the nucleotide sequence, or the whole or part of the nucleotide sequence with a deletion, substitution, or addition of one or several nucleotides is preferably amplified. In this case, the number of nucleotides in the oligonucleotide is not particularly limited, and the number is preferably 13 to 30, more preferably 18 to 23.

In order to detect *Paecilomyces variotii* by performing an amplification reaction by the PCR method, the following oligonucleotide (c) or oligonucleotide (d) are preferably used as nucleic acid primers, and the oligonucleotide represented by the nucleotide sequence set forth in SEQ ID NO: 5 and the oligonucleotide represented by the nucleotide sequence set forth in SEQ ID NO: 6 are more preferably used.

(c) An oligonucleotide represented by the nucleotide sequence set forth in SEQ ID NO: 5, or an oligonucleotide represented by a nucleotide sequence which has 70% or more homology to the nucleotide sequence set forth in SEQ ID NO: 5 and can be used as a nucleic acid primer (d) An oligonucleotide represented by the nucleotide sequence set forth in SEQ ID NO: 6, or an oligonucleotide represented by a nucleotide sequence which has 70% or more homology to the nucleotide sequence set forth in SEQ ID NO: 6 and can be used as a nucleic acid primer Further, the oligonucleotide pair for detecting *Paecilomyces variotii* of the present invention is a pair of oligonucleotides consisting of the oligonucleotide (c) and the oligonucleotide (d).

The oligonucleotides of SEQ ID NO: 5 and SEQ ID NO: 6 are present in the β-tubulin gene region of *Paecilomyces*

*variotii* and have nucleotide sequences identical to a partial nucleotide sequence of the variable region or complementary sequences thereof. These oligonucleotides can hybridize specifically with part of the DNA of *Paecilomyces variotii*.

The oligonucleotides (c) and (d) correspond to the region of the position 64 to 85 and the region of the position 306 to 325, respectively, in the nucleotide sequence set forth in SEQ ID NO: 1. Therefore, when the oligonucleotides are hybridized with the β-tubulin gene of *Paecilomyces variotii*, *Paecilomyces variotii* can be specifically detected.

Further, in the present invention, in order to detect *Paecilomyces variotii* by performing an amplification reaction by the PCR method, the following oligonucleotide (e), and the oligonucleotide (f) and/or oligonucleotide (g) are preferably used as nucleic acid primers; the oligonucleotide represented by the nucleotide sequence set forth in SEQ ID NO: 7, and the oligonucleotide represented by the nucleotide sequence set forth in SEQ ID NO: 8 and/or the oligonucleotide represented by the nucleotide sequence set forth in SEQ ID NO: 9 are more preferably used; and the oligonucleotide represented by the nucleotide sequence set forth in SEQ ID NO: 7, the oligonucleotide represented by the nucleotide sequence set forth in SEQ ID NO: 8 and the oligonucleotide represented by the nucleotide sequence set forth in SEQ ID NO: 9 are particularly preferably used.

(e) An oligonucleotide represented by the nucleotide sequence set forth in SEQ ID NO: 7, or an oligonucleotide represented by a nucleotide sequence which has 70% or more homology to the nucleotide sequence set forth in SEQ ID NO: 7 and can be used as a nucleic acid primer;

(f) An oligonucleotide represented by the nucleotide sequence set forth in SEQ ID NO: 8, or an oligonucleotide represented by a nucleotide sequence which has 70% or more homology to the nucleotide sequence set forth in SEQ ID NO: 8 and can be used as a nucleic acid primer; and (g) An oligonucleotide represented by the nucleotide sequence set forth in SEQ ID NO: 9, or an oligonucleotide represented by a nucleotide sequence which has 70% or more homology to the nucleotide sequence set forth in SEQ ID NO: 9 and can be used as a nucleic acid primer.

Further, the oligonucleotide pair (oligonucleotide group) for detecting *Paecilomyces variotii* of the present invention is a pair of oligonucleotides consisting of the oligonucleotide (e) and the oligonucleotide (f), a pair of oligonucleotides consisting of the oligonucleotide (e) and the oligonucleotide (g), or a group of oligonucleotides consisting of the oligonucleotide (e), the oligonucleotide (f) and the oligonucleotide (g).

The oligonucleotides of SEQ ID NO: 7, SEQ ID NO: 8 and SEQ ID NO: 9 are oligonucleotides having nucleotide sequences which are present in the β-tubulin gene region of *Paecilomyces variotii* and have nucleotide sequences identical to a partial nucleotide sequence of the variable region or complementary sequences thereof. These oligonucleotides can hybridize specifically with part of DNA of *Paecilomyces variotii*.

The oligonucleotides (e) and (f) correspond to the region of the position 98 to 116 and the region of the position 266 to 285, respectively, in the nucleotide sequence set forth in SEQ ID NO: 22. The oligonucleotides (e) and (g) correspond to the region of the position 92 to 110 and the region of the position 261 to 280, respectively, in the nucleotide sequence set forth in SEQ ID NO: 28.

Therefore, when the oligonucleotides are hybridized with the β-tubulin gene of *Paecilomyces variotii*, *Paecilomyces variotii* can be specifically detected.

Conditions of the PCR reaction in the present invention are not particularly limited as long as a DNA fragment of interest can be amplified to a detectable degree. A preferred example of the PCR reaction conditions is as follows. A cycle including: a thermal denaturation reaction for denaturation of double-stranded DNA into single strands at 95 to 98° C. for 10 to 60 seconds; an annealing reaction for hybridization of a primer pair with the single-stranded DNA at about 59° C. for about 60 seconds; and an elongation reaction for a reaction of a DNA polymerase at about 72° C. for about 60 seconds is repeated about 30 to 35 times.

In the present invention, confirmation of gene fragments amplified by the PCR method can be performed by a usual method. Examples of the method include, but not limited to, a method of integrating a nucleotide labeled with a radioactive substance or the like in an amplification reaction, a method including performing electrophoresis for PCR reaction products and confirming the existence of a band corresponding to the size of the amplified gene, a method of determining the nucleotide sequences of PCR reaction products, and a method of integrating a fluorescent substance into between the double strands of amplified DNA. In the present invention, the method including performing electrophoresis after a gene amplification treatment and confirming the existence of a band corresponding to the size of the amplified gene is preferred.

In the case where a sample contains *Paecilomyces variotii*, amplification of DNA fragments specific to the fungus can be observed by performing a PCR reaction using the oligonucleotide pair of the present invention as a primer set and performing electrophoresis for the resultant PCR reaction products.

Specifically, in the case of using the oligonucleotides (c) and (d) as nucleic acid primers, amplification of a DNA fragment of about 250 bp is observed; while in the case of using the oligonucleotide (e), and the oligonucleotide (f) and/or the oligonucleotide (g) as nucleic acid primers, amplification of a DNA fragment of about 200 bp is observed. The procedure can confirm whether the sample contains *Paecilomyces variotii* or not.

In the present invention, in the case where a DNA fragment including the variable region is amplified by the LAMP method, an isothermal complementary strand synthesis reaction can be performed because periodic temperature control is not required. Therefore, a specific fungus in a sample can be detected easily and rapidly.

The LAMP method is a loop-mediated isothermal amplification method which does not require the periodic temperature control essential for the PCR method (WO 00/28082 A1), which allows isothermal complementary strand synthesis reactions by annealing the 3'-end side of a primer to a nucleotide serving as a template to prepare a starting point of complementary strand synthesis and combining a primer that anneals to a loop formed at this time. In the LAMP method, at least four primers which recognize six nucleotide sequence regions of the nucleic acid serving as a template are required. The primers are designed so that the 3'-end side is certainly annealed to the nucleotide serving as a template, and hence a checking mechanism based on complementary binding of the nucleotide sequences functions repeatedly, which enables a sensitive and specific nucleic acid amplification reaction.

Six nucleotide sequence regions recognized by primers to be used in the LAMP method are referred to as F3, F2 and F1 in this order from the 5'-end side of a nucleotide serving as a template, and B3c, B2c and B1c in this order from the 3'-end side. Complementary sequences of F1, F2 and F3 are called F1c, F2c and F3c, respectively. Complementary sequences of B1c, B2c and B3c are called B1. B2 and B3, respectively.

While the six nucleotide sequence regions may be selected by the following procedure, the present invention is not limited thereto.

Alignment of a nucleotide sequence of a gene of a fungus of interest is performed, and a plurality of primers are designed using software such as Primer Explorer V4 (HP of Eiken Chemical Co., Ltd.). The primers are synthesized and used in actual LAMP reactions, and primers which can specifically detect *Paecilomyces variotii* are adopted.

The details are as follows.
1. An alignment file of nucleotide sequence information of a target region of a fungus of interest is created using alignment software such as Clustal X.
2. Primers are designed based on the information of the alignment file using Primer Explorer V4 (HP of Eiken Chemical Co., Ltd.).
3. A set of primers which are more stable (which hardly have a dimer structure) and include many mutations on the edge of the elongation direction (species-specific mutations) is selected from designed primer set candidates. In particular, an inner primer including many mutations in the elongation direction increases the probability of differentiation from related species. In the case where primer set candidates cannot be created, design is performed so that the scope of the Tm value or the number of nucleotides in a primer is expanded.
4. A test is actually performed using the selected primer set to confirm the effectiveness. After confirmation of the effectiveness, loop primers are designed to shorten the reaction time.

Primers to be used in the LAMP method are designed by first determining the above-mentioned six nucleotide sequence regions from the nucleotide sequence of the target region, and then designing inner primers F and B and outer primers F and B to be described below.

The inner primer used in the LAMP method is an oligonucleotide having, at the 3' end, a nucleotide sequence that recognizes a certain nucleotide sequence region in a target nucleotide sequence and provides a synthesis origin; and having, at the 5' end, a nucleotide sequence complementary to an arbitrary region of a nucleic acid synthesis reaction product obtained with this primer at the origin. In this context, a primer containing a "nucleotide sequence selected from F2" at the 3' end and a "nucleotide sequence selected from F1c" at the 5' end is called an inner primer F (hereinafter, abbreviated to FIP), and a primer containing a "nucleotide sequence selected from B2" at the 3' end and a "nucleotide sequence selected from B1c" at the 5' end is called an inner primer B (hereinafter, abbreviated to BIP). The inner primers may have arbitrary nucleotide sequences including 0 to 50 nucleotides at a position between the F2 region and the F1c region or between the B2 region and the B1c region.

On the other hand, the "outer primer" is an oligonucleotide having a nucleotide sequence that recognizes a "certain nucleotide sequence region present on the 5'-end side of "a certain nucleotide sequence region" (e.g., the above-mentioned F2 region or B2 region)" in the target nucleotide sequence and provides a synthesis origin. Examples thereof include a primer including a nucleotide sequence selected from the F3 region and a primer including a nucleotide sequence selected from the B3 region. In this context, a primer containing a "nucleotide sequence selected from F3" is called an outer primer F (hereinafter, abbreviated to F3), and a primer containing a "nucleotide sequence selected from B3" is called an outer primer B (hereinafter, abbreviated to B3).

In this context, "F" in each primer indicates that the primer complementarity binds to the anti-sense strand of the target nucleotide sequence and provides a synthesis origin. On the other hand, "B" in each primer indicates that the primer complementarily binds to the sense strand of the target nucleotide sequence and provides a synthesis origin.

In the amplification of the nucleic acid by the LAMP method, a loop primer(s) (hereinafter, abbreviated to LF and LB) can be preferably used in addition to the inner and outer primers. The loop primers refer to 2 primers (one for each of strands composing a double-strand) containing, at the 3' end, a nucleotide sequence complementary to a sequence in a loop formed by the annealing of complementary sequences present at the same strand of an amplification product obtained by the LAMP method. That is, the loop primer is a primer having a nucleotide sequence complementary to a nucleotide sequence of a single strand moiety of the loop structure on the 5'-end side in the dumbbell-like structure. The use of the loop primers increases nucleic acid synthesis origins in number and achieves reduction in reaction time and enhancement in detection sensitivity (WO 02/24902 Pamphlet).

The nucleotide sequence of the loop primer may be selected from nucleotide sequences in the target region or complementary strands thereof as long as the sequence is complementary to the nucleotide sequence of the single strand moiety of the loop structure on the 5'-end side in the dumbbell-like structure, or may be another nucleotide sequence. Further, one type or two types of loop primers may be used.

When a DNA fragment including the target region is amplified using at least four or more types of the above-mentioned primers, the DNA fragment can be amplified to an amount sufficient for specific and efficient detection of the DNA fragment. Therefore, a specific fungus can be detected by confirming whether the amplified product is present or not.

The primer which can be used for the LAMP method preferably includes 15 or more nucleotides, more preferably 20 or more nucleotides. Further, each primer may be an oligonucleotide of single nucleotide sequence or a mixture of oligonucleotides of a plurality of nucleotide sequences.

Further, the outer primer which can be used for the LAMP method may be used in the PCR method for amplifying a DNA fragment including a target region. In the PCR method, a DNA fragment of interest can be amplified by PCR using the above-mentioned primers, the β-tubulin gene in a sample as a template, and a heat-stable DNA polymerase.

Hereinafter, primer sets which are preferably used in detection of *Paecilomyces variotii* by the LAMP method are described. To specifically detect *Paecilomyces variotii*, the following primer set (primer set 1) is more preferably used.

Primer Set 1 for Detecting *Paecilomyces variotii*

```
LPae1F3 primer:
                                    (SEQ ID NO: 10)
ACGATCCTATAGGCAGACCA LPae1B3 primer:
                                    (SEQ ID NO: 11)
CCAGCGGCCTATTTATTGGT LPae1FIP primer:
                                    (SEQ ID NO: 12)
CGTCTCTCTCGATTCCGTGTCGCCTTGACGGCTCTGGTGT
```

```
LPae1BIP primer:
                                    (SEQ ID NO: 13)
CTCCGACCTTCAGCTCGAGCGGAGCGTTCCTCTTGGGAT
```

To detect *Paecilomyces variotii*, loop primers are preferably used in addition to the above-mentioned primers. The following primers are preferably used as the loop primers.
Loop Primers for Detecting *Paecilomyces variotii*

```
                                    (SEQ ID NO: 14)
LPae1LF loop primer: TCCCCAGATATCGTGTACTTAC (SEQ ID NO: 15)
LPae1LB loop primer: ACTTCAACGAGGTAGTTGTTG
```

FIG. 1 illustrates the position relationship of nucleotide sequences recognized by the above-mentioned primers in the nucleotide sequence of the β-tubulin gene of *Paecilomyces variotii* IFM40913 strain.

In the present invention, the following primer set (primer set 2) is also preferably used in detection of *Paecilomyces variotii* by the LAMP method.
Primer Set 2 for Detecting *Paecilomyces variotii*

```
LPae2F3 primer:
                                    (SEQ ID NO: 16)
CGATATCTGGGGATGCTTCG LPae2B3 primer:
                                    (SEQ ID NO: 17)
CGTCCATGGTACCAGGCT LPae2FIP primer:
                                    (SEQ ID NO: 18)
ATGCGCTCGAGCTGAAGGTCCGGAATCGAGAGAGAGACGACT LPae2BIP primer:
                                    (SEQ ID NO: 19)
TGATCCCAAGAGGAACGCCCCACGAGGAACGTACTTCTTGCC
```

To detect *Paecilomyces variotii*, loop primers are preferably used in addition to the above-mentioned primers. The following primers are preferably used as the loop primers.
Loop Primers for Detecting *Paecilomyces variotii*

```
                                    (SEQ ID NO: 20)
LPae2LF loop primer: GGAGGAGCCATTGTAGCTAA (SEQ ID NO: 21)
LPae2LB loop primer: GAGCTCACCAATAAATAGGCC
```

FIG. 2 illustrates the position relationship of nucleotide sequences recognized by the above-mentioned primers in the nucleotide sequence of the β-tubulin gene of *Paecilomyces variotii* IFM40913 strain and *Paecilomyces variotii* IFM40915 strain.

The primer set for detecting *Paecilomyces variotii* of the present invention is a primer set to be used for detection by the LAMP method and includes a primer consisting of an oligonucleotide represented by the nucleotide sequence set forth in SEQ ID NO: 10, a primer consisting of an oligonucleotide represented by the nucleotide sequence set forth in SEQ ID NO: 11, a primer consisting of an oligonucleotide represented by the nucleotide sequence set forth in SEQ ID NO: 12 and a primer consisting of an oligonucleotide represented by the nucleotide sequence set forth in SEQ ID NO: 13; and the primer set preferably further includes primers consisting of oligonucleotides represented by the nucleotide sequences set forth in SEQ ID NO: 14 and SEQ ID NO: 15.

The another primer set for detecting *Paecilomyces variotii* of the present invention is a primer set to be used for detection by the LAMP method and includes a primer consisting of an oligonucleotide represented by the nucleotide sequence set forth in SEQ ID NO: 16, a primer consisting of an oligonucleotide represented by the nucleotide sequence set forth in SEQ ID NO: 17, a primer consisting of an oligonucleotide represented by the nucleotide sequence set forth in SEQ ID NO: 18 and a primer consisting of an oligonucleotide represented by the nucleotide sequence set forth in SEQ ID NO: 19; and the primer set preferably further includes primers consisting of oligonucleotides represented by the nucleotide sequences set forth in SEQ ID NO: 20 and SEQ ID NO: 21.

When the above-described primer set is used, a DNA fragment including a target region of the β-tubulin gene of *Paecilomyces variotii* can be amplified specifically, rapidly, and sensitively by the LAMP method. Therefore, the existence of *Paecilomyces variotii* in a sample can be determined by confirming amplification of the DNA fragment.

Further, the oligonucleotide for detecting *Paecilomyces variotii* of the present invention is preferably an oligonucleotide represented by a nucleotide sequence corresponding to any one of the following (a') to (f') when nucleotide sequence regions F3, F2 and F1 are selected from the 5'-end side in a target region selected from the nucleotide sequence of the β-tubulin gene, nucleotide sequence regions B3c, B2c and B1c are selected from the 3'-end side in the target region, complementary nucleotide sequences of the B3c, B2c and B1c are called B3, B2 and B1, respectively, and complementary nucleotide sequences of the F3, F2 and F1 are called F3c, F2c and B1c, respectively.

(a') A nucleotide sequence having the sequence identical to that of the B2 region at the 3' terminal side and the sequence identical to that of the B1c region at the 5' terminal side (b') A nucleotide sequence having the sequence identical to that of the B3 region (c') A nucleotide sequence having the sequence identical to that of the F2 region at the 3' terminal side and the sequence identical to that of the F1c region at the 5' terminal side (d') A nucleotide sequence having the sequence identical to that of the F3 region (e') A nucleotide sequence having a sequence complement to a part between the B1 region and the B2 region (f') A nucleotide sequence having a sequence complement to a part between the F1 region and the F2 region The oligonucleotide of the present invention may be used not only as a primer for the LAMP method but also as, for example, a primer for the PCR method or a probe for detecting a nucleic acid.

An enzyme used in amplification of the DNA fragment including the target region by LAMP method is not particularly limited as long as it is generally used, and it is preferably a template-dependent nucleic acid synthetase having strand displacement activities. Such an enzyme includes Bst DNA polymerase (large fragment), Boa (exo-) DNA polymerase, and the Klenow fragment of *E. coli* DNA polymerase I; and preferably includes Bst DNA polymerase (large fragment). The enzyme that can be used in the present invention may be purified from viruses, bacteria, or the like or may be prepared by a gene recombination technique. These enzymes may be modified by fragmentation, amino acid substitution, or the like.

The temperature for amplification of the DNA fragment including the target region by the LAMP method is not particularly limited but is preferably 55 to 68° C., more preferably 60 to 65° C.

The amplification of the DNA fragment including the target region can be confirmed by general method. For example, in the case of amplifying the DNA fragment including the target region by the LAMP method, the nucleic acid amplification products can be detected by hybridization of a labeled oligonucleotide specifically recognizing amplified nucleotide sequences or a fluorescent intercalator method (JP-A-2001-242169), or can be detected by directly applying the reaction solution after the completion of reaction to agarose gel electrophoresis. In the agarose gel electrophoresis, the LAMP amplification products are detected in the form of a ladder of many bands differing in base length.

Moreover, in the LAMP method, substrates are consumed in large amounts by nucleic acid synthesis, and pyrophosphoric acid ions as by-products are converted into magnesium pyrophosphate through its reaction with coexisting magnesium ions and makes the reaction solution cloudy to the extent that can be observed visually. Thus, the nucleic acid amplification reaction may be detected by confirming this cloudiness by use of a measurement apparatus that can optically observe time-dependent rises in turbidity after the completion of reaction or during reaction, for example, by confirming changes in absorbance at 400 nm by use of a usual spectrophotometer (WO 01/83817 Pamphlet).

In the present invention, primers to be used for amplifying the DNA fragment including the target region may be chemically synthesized based on designed sequences or purchased from a manufacturer of reagents. Specifically, the primers may be synthesized using an oligonucleotide synthesizer or the like. Moreover, after synthesis, the oligonucleotides may be purified by an adsorption column, high-performance liquid chromatography, or electrophoresis before use. Furthermore, an oligonucleotide having a nucleotide sequence with a substitution, deletion, insertion, or addition of one or several nucleotides may be synthesized by a known method.

The sample to be used in the present invention is not particularly limited and may be a food or drink itself, a raw material of the food or drink, an isolated fungus, a cultured fungus, or the like.

A method of preparing DNA from a sample is not particularly limited as long as DNA can be obtained at a sufficient purification degree and in a sufficient amount for detecting *Paecilomyces variotii*. While the sample may be used without purification, the sample may be subjected to a pre-treatment such as separation, extraction, concentration, or purification before use. For example, the sample may be purified by phenol and chloroform extraction or using a commercially available extraction kit to increase the purity of the nucleic acid before use. Moreover, DNA obtained by reverse transcription of RNA in a sample may be used.

A variety of reagents necessary for amplification of the DNA fragment including the target region using the primer of the present invention may be packaged as a kit in advance.

For example, the kit of the present invention includes the above-mentioned primer set which may be used in the LAMP method (preferably, the primer set which includes the primers consisting of each of the oligonucleotides represented by the nucleotide sequences set forth in SEQ ID NOS: 10 to 13, the primer set which includes the primers consisting of each of the oligonucleotides represented by the nucleotide sequences set forth in SEQ ID NOS: 10 to 15, the primer set which includes the primers consisting of each of the oligonucleotides represented by the nucleotide sequences set forth in SEQ ID NOS: 16 to 19, or the primer set which includes the primers consisting of each of the oligonucleotides represented by the nucleotide sequences set forth in SEQ ID NOS: 16 to 21), a DNA polymerase, and dNTPs consisting of dATP, dCTP, dGTP, and dTTP. The kit preferably includes the above-mentioned primer set, a variety of oligonucleotides necessary as loop primers (preferably primers consisting of the oligonucleotides represented by the nucleotide sequences set forth in SEQ ID NOS: 7 and 8), four types of dNTPs serving as substrates of nucleic acid synthesis (dATP, dCTP, dGTP, and dTTP), a DNA polymerase such as a template-dependent nucleic acid synthetase having strand displacement activity, a buffer which provides preferred conditions for enzymatic reactions, a salt serving as a cofactor (such as a magnesium salt or a manganese salt), and a protecting agent for stabilizing an enzyme or a template, and if necessary, reagents necessary for detection of reaction products. The kit of the present invention may include a positive control for confirming whether the LAMP reaction proceeds normally by the primers of the present invention. The positive control is, for example, DNA including a region which is amplified by the method of the present invention.

Further, the kit for detecting *Paecilomyces variotii* of the present invention includes, as nucleic acid primers, an oligonucleotide pair or an oligonucleotide group, which includes at least one pair or one group selected from the group consisting of a pair of the oligonucleotides (c) and (d), a pair of the oligonucleotides (e) and (f), a pair of the oligonucleotides (e) and (g), or a group of the oligonucleotides (e), (f) and (g). The kit can be preferably used in the method of detecting *Paecilomyces variotii* by the PCR method. The kit of the present invention may include not only the above-mentioned nucleic acid primers but also, depending on purpose, substances which are usually used for detecting a fungus, such as a label-detecting substance, a buffer, a nucleic acid synthetase (such as a DNA polymerase, an RNA polymerase, or a reverse transcriptase), and an enzyme substrate (such as dNTP or rNTP). The kit of the present invention may include a positive control for confirming whether the PCR reaction proceeds normally by the primers of the present invention. The positive control is, for example, DNA including a region which is amplified by the method of the present invention.

According to the method of the present invention, a procedure from a sample preparation step to a fungus detection step can be performed within a time as short as about 60 to 120 minutes.

EXAMPLES

Hereinafter, the present invention will be described more in detail with reference to Examples, but it should be understood that the technological scope of the present invention is not particularly limited by the following Examples.

Example 1

Detection of *Paecilomyces variotii* by PCR Method (1) Analysis of Target Gene

The nucleotide sequence of the β-tubulin gene of *Paecilomyces variotii* was determined by the following method.

A test fungus was cultured in the dark on a potato dextrose agar slant at 25° C. for 7 days. DNA was extracted from the fungus using GenTorukun™ (manufactured by TAKARA BIO INC.). PCR amplification of a target site was performed using PuRe Taq™ Ready-To-Go PCR Beads (manufactured by GE Health Care UK LTD) and, as primers, Bt2a (5'-GGTAACCAAATCGGTGCTGCTTTC-3', SEQ ID NO: 34) and Bt2b (5'-ACCCTCAGTGTAGTGACCCTTGGC-3', SEQ ID NO: 35) (Glass and Donaldson, Appl Environ Microbiol 61:1323-1330, 1995). Amplification of β-tubulin partial length was performed under conditions including a denaturation temperature of 95° C., an annealing temperature of 59° C., an elongation temperature of 72° C., and 35 cycles. PCR products were purified using Auto Seg™ G-50 (manufactured by Amersham Pharmacia Biotech). The PCR products were labeled with BigDye (registered trademark) terminator Ver. 1.1 (manufactured by Applied Biosystems), and electrophoresis was performed using ABI PRISM 3130 Genetic Analyzer (manufactured by Applied Biosystems). Nucleotide sequences from fluorescence signals in electrophoresis were determined using the software "ATGC Ver. 4" (manufactured by Genetyx).

(2) Preparation of Primers

Based on the β-tubulin sequence of *Paecilomyces variotii* determined as above, the β-tubulin sequences of *Hamigera avellanea*, *Talaromyces flavus*, *Talaromyces luteus*, *Talaromyces trachyspermus*, *Byssochlamys nivea* and *Byssochlamys fulva* determined in the same way as above, and known β-tubulin sequences of a variety of fungi, alignment analyses were performed using DNA analysis software (Clustal W), to thereby determine nucleotide sequences specific to *Paecilomyces variotii* (SEQ ID NOS: 1 to 4 and 22 to 33). From regions having particularly high specificity to *Paecilomyces variotii* on the 3'-end side in the determined regions, partial regions which satisfy the following four conditions were searched:

1) the partial region includes several nucleotides specific to the species;
2) the partial region has a GC content of about 30% to 80%;
3) the partial region has low possibility to cause self-annealing; and
4) the partial region has a Tm value of about 55 to 65° C.

Based on the nucleotide sequences, five primer pairs including primers which consist of each of the oligonucleotides represented by the nucleotide sequences set forth in SEQ ID NOS: 5 and 6 were designed. Then, the primers were synthesized by Sigma-Aldrich Japan (desalted products, 0.02 μmol scale) and purchased.

(3) Preparation of Samples

The fungi shown in Tables 1 and 2 were used as fungi to be used for evaluation of the effectiveness of the designed primers, i.e., *Paecilomyces variotii*, other heat-resistant fungi, and general fungi. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. (for general fungi) or 30° C. (for heat-resistant fungi) for 7 days.

TABLE 1

| Sample No. | Scientific name | Strain No. (IFM) |
|---|---|---|
| 1 | Paecilomyces varioti | IFM40913 |
| 2 | Paecilomyces varioti | IFM40915 |
| 3 | Byssochlamys fluva | IFM48421 |
| 4 | Byssochlamys fluva | IFM51213 |
| 5 | Byssochlamys nivea | IFM51244 |
| 6 | Byssochlamys nivea | IFM51245 |
| 7 | Hamigera avellanea | IFM42323 |
| 8 | Hamigera avellanea | IFM52241 |
| 9 | Talaromyces flavus | IFM42243 |
| 10 | Talaromyces flavus | IFM52233 |
| 11 | Talaromyces luteus | IFM53242 |
| 12 | Talaromyces luteus | IFM53241 |

TABLE 1-continued

| Sample No. | Scientific name | Strain No. (IFM) |
|---|---|---|
| 13 | Talaromyces trachyspermus | IFM42247 |
| 14 | Talaromyces trachyspermus | IFM52252 |
| 15 | Talaromyces wortmannii | IFM52255 |
| 16 | Talaromyces wortmannii | IFM52262 |

TABLE 2

| Sample No. | Scientific name | Strain No. (IFM) |
|---|---|---|
| 1 | Paecilomyces varioti | IFM40913 |
| 2 | Paecilomyces varioti | IFM40915 |
| 3 | Byssochlamys nivea | IFM50292 |
| 4 | Neosartorya ficheri | IFM46945 |
| 5 | Neosartorya spinosa | IFM46967 |
| 6 | Neosartorya glabra | IFM46949 |
| 7 | Neosartorya hiratsukae | IFM47036 |
| 8 | Aspergillus fumigatus | A125 |
| 9 | Aspergillus niger | An25 |
| 10 | Aspergillus terreus | A229 |
| 11 | Aspergillus flavus | As17 |
| 12 | Emericella nidulans | As18 |
| 13 | Penicillium griseofulvum | IFM54313 |
| 14 | Penicillium citirinum | IFM54314 |
| 15 | Alternaria alternate | IFM41348 |
| 16 | Aureobasidium pullulans | IFM41409 |
| 17 | Chaetomium globosum | IFM40869 |
| 18 | Fusarium oxysporum | IFM50002 |
| 19 | Trichoderma viride | IFM40938 |
| 20 | Cladosporium cradosporioides | IFM41450 |

(4) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/μL.

(5) PCR Reaction

One μL of the genomic DNA solution prepared above as a DNA template, 13 μL of Pre Mix Taq (trade name, manufactured by TAKARA BIO INC.) and 10 μL of sterile distilled water were mixed, and 0.5 μL of a forward primer (20 pmol/μL) such as a primer consisting of an oligonucleotide represented by the nucleotide sequence set forth in SEQ ID NO: 5 (Pae1F primer) and 0.5 μL of a reverse primer (20 pmol/μL) such as a primer consisting of an oligonucleotide represented by the nucleotide sequence set forth in SEQ ID NO: 6 (Pae1R primer) were added thereto, to thereby prepare 25 μL of a PCR reaction solution.

The PCR reaction solution was subjected to a gene amplification treatment using an automatic gene amplification device thermal cycler DICE (TAKARA BIO INC.). PCR reaction conditions were 30 cycles of (i) a thermal denaturation reaction at 98° C. for 10 seconds, (ii) an annealing reaction at 63° C. for 1 minute, and (iii) an elongation reaction at 72° C. for 1 minute.

(6) Confirmation of Amplified Gene Fragment

After the PCR reaction, 10 μL of a sample was collected from the PCR reaction solution and electrophoresed using a 2% agarose gel, and DNA was stained with SYBR Safe DNA gel stain in 1×TAE (Invitrogen), followed by fluorescence detection under ultraviolet light, to thereby confirm whether the amplified DNA fragment was present or not. As a result, in the case of using the primer pair including the oligonucleotides represented by the nucleotide sequences set forth in SEQ ID NOS: 5 and 6 of the designed five primer sets, in a sample containing genomic DNA of *Paecilomyces variotii*, amplification of gene fragments was confirmed at a position corresponding to the size expected from the designed primer pairs. On the other hand, in a sample containing no genomic DNA of *Paecilomyces variotii*, amplification of gene fragments was not confirmed. FIG. 3 and FIG. 4 show an electrophoretogram in the agarose gel in the case of using the primer pair including the oligonucleotides represented by the nucleotide sequences set forth in SEQ ID NOS: 5 and 6. Note that, FIG. 3 shows an electrophoretogram of samples of the fungi shown in Table 1, and FIG. 4 shows an electrophoretogram of samples of the fungi shown in Table 2. The numbers in the electrophoretograms represent samples which were subjected to reactions using DNAs extracted from samples of the corresponding sample numbers in the tables.

As a result, in the case of the samples containing the genomic DNA of *Paecilomyces variotii*, amplification of gene fragments of about 250 bp was confirmed. On the other hand, in the case of the samples containing no genomic DNA of *Paecilomyces variotii*, amplification of gene fragments was not confirmed.

The above-described results reveal that *Paecilomyces variotii* can be specifically detected by using the oligonucleotides of the present invention set forth in SEQ ID NOS: 5 and 6. Moreover, the results reveal that it is possible to easily design oligonucleotides for detecting *Paecilomyces variotii*, which can act as nucleic acid probes or nucleic acid primers for specifically detecting *Paecilomyces variotii*, based on the nucleotide sequence of the variable region of the β-tubulin gene of the present invention.

Example 2

Detection of *Paecilomyces variotii* by LAMP Method (1) Design and Synthesis of Primers Based on the nucleotide sequence regions which were specified in Example 1 above and specific to *Paecilomyces variotii* (SEQ ID NOS: 1 to 4 and 22 to 33), primers consisting of each of oligonucleotides represented by the nucleotide sequences set forth in SEQ ID NOS: 10 to 15 were designed, and the primers were synthesized by E Genome order (FUJITSU SYSTEM SOLUTIONS LIMITED, SEQ ID NOS: 10 and 11; 5 μmol scale, SEQ ID NOS: 12 and 13; 40 μmol scale, SEQ ID NOS: 14 and 15: 20 μmol scale; all of the primers are column-purified products) and purchased.

(2) Preparation of Samples

The fungi shown in Table 3 were used as fungi to be used for evaluation of the effectiveness of the designed primers, i.e., *Paecilomyces variotii* and other heat-resistant fungi. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 30° C. for 7 days.

TABLE 3

| Sample No. | Scientific name | Strain No. (IFM) |
| --- | --- | --- |
| 1 | *Paecilomyces varioti* | IFM40913 |
| 2 | *Paecilomyces varioti* | IFM40915 |
| 3 | *Byssochlamys fluva* | IFM48421 |

TABLE 3-continued

| Sample No. | Scientific name | Strain No. (IFM) |
| --- | --- | --- |
| 4 | *Byssochlamys nivea* | IFM51244 |
| 5 | *Hamigera avellanea* | IFM42323 |
| 6 | *Talaromyces flavus* | IFM42243 |
| 7 | *Talaromyces luteus* | IFM53242 |
| 8 | *Talaromyces wortmannii* | IFM52255 |

(3) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). Specifically, several colonies were collected from each medium, and the fungus was suspended in 200 μL of a reagent supplied with the kit and dissolved by a heat treatment at 100° C. for 10 minutes. Centrifugation was performed at 14,800 rpm for 5 minutes, and the supernatant was collected. The concentration of the resultant genomic DNA solution was adjusted to 50 ng/μL. The genomic DNA solution was used as a template DNA in the following LAMP reaction.

(4) Preparation of Reaction Solution for LAMP Reaction 12.5 μL of 2× Reaction Mix (Tris-HCl (pH 8.8) 40 mM, KCl 20 mM, MgSO$_4$ 16 mM, (NH$_4$)$_2$SO$_4$ 20 mM, 0.2% Tween20, Betaine 1.6 M, dNTPs 2.8 mM: Eiken Chemical Co., Ltd.; Loopamp DNA amplification reagent kit), 1 μL of a primer consisting of an oligonucleotide represented by the nucleotide sequence set forth in SEQ ID NO: 10 (LPae1F3 primer: 5 pmol/μL), 1 μL of a primer consisting of an oligonucleotide represented by the nucleotide sequence set forth in SEQ ID NO: 11 (LPae1B3 primer: 5 pmol/μL), 1 μL of a primer consisting of an oligonucleotide represented by the nucleotide sequence set forth in SEQ ID NO: 12 (LPae1FIP primer: 40 pmol/μL), 1 μL of a primer consisting of an oligonucleotide represented by the nucleotide sequence set forth in SEQ ID NO: 13 (LPae1BIP primer: 40 pmol/μL), 1 μL of a primer consisting of an oligonucleotide represented by the nucleotide sequence set forth in SEQ ID NO: 14 (LPae1LF loop primer: 20 pmol/μL), 1 μL of a primer consisting of an oligonucleotide represented by the nucleotide sequence set forth in SEQ ID NO: (LPae1LB loop primer: 20 pmol/μL), 1 μL of Bst DNA Polymerase (8 U/25 μL, manufactured by Eiken Chemical Co., Ltd.) and 1 μL of the template DNA prepared above were mixed, and distilled water was added thereto, to thereby prepare a total of 25 μL of a reaction solution.

(5) LAMP Reaction

The reaction solution prepared above was subjected to a DNA amplification reaction at 63±2° C. for 60 minutes using a real-time turbidity measuring apparatus Loopamp RT-160C (manufactured by Eiken Chemical Co., Ltd.). Simultaneously, the turbidity of the reaction solution was measured (wavelength: 400 nm).

(6) Confirmation of DNA Amplification

Figure 5:
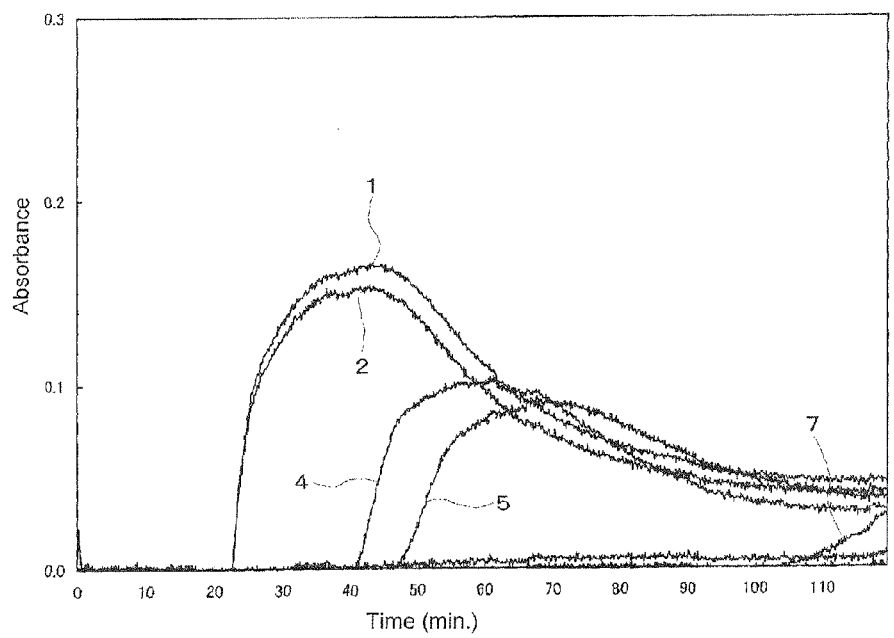
[FIG. 5]

Amplification of DNA was judged to be present or not by whether or not the turbidity increased in the reaction solution. The measurement results of the turbidity of the reaction solutions are shown in FIG. 5.

As a result, the turbidity increases, that is, the DNA synthesis and amplification reactions were observed from about 23 minutes after the initiation of the reaction only in the systems where the genomic DNAs of *Paecilomyces variotii* were used as templates.

On the other hand, in the systems where the genomic DNAs of other fungi were used, the turbidity increases in the reaction solutions were not observed for 40 minutes after the initiation of the reaction. Note that, also in the systems where the genomic DNAs of fungi other than *Paecilomyces variotii* were used, the turbidity increases of the reaction solutions were observed from about 45 minutes after the initiation of the reaction. However, the phenomena are probably caused by time-dependent occurrence of a nonspecific reaction among primers or by a reaction of a small amount of primers to sites other than the target due to a long reaction time.

Example 3

Detection of *Paecilomyces variotii* by LAMP Method (1) Design and Synthesis of Primers Based on the nucleotide sequence regions which were specified in Example 1 above and specific to *Paecilomyces variotii* (SEQ ID NOS: 1 to 4 and 22 to 33), primers consisting of each of oligonucleotides represented by the nucleotide sequences set forth in SEQ ID NOS: 16 to 21 were designed, and the primers were synthesized by E Genome order (FUJITSU SYSTEM SOLUTIONS LIMITED, SEQ ID NOS: 16 and 17; 5 μmol scale, SEQ ID NOS: 18 and 19; 40 pmol scale, SEQ ID NOS: 20 and 21: 20 μmol scale; all of the primers are column-purified products) and purchased.

(2) Preparation of Samples

The fungi shown in Table 4 were used as fungi to be used for evaluation of the effectiveness of the designed primers, i.e., *Paecilomyces variotii*, other heat-resistant fungi, and general fungi. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. (for general fungi) or 30° C. (for heat-resistant fungi) for 7 days.

TABLE 4

| Sample No. | Scientific name | Strain No. (IFM) |
|---|---|---|
| 1 | *Paecilomyces varioti* | IFM40913 |
| 2 | *Paecilomyces varioti* | IFM40915 |
| 3 | *Byssochlamys fluva* | IFM48421 |
| 4 | *Hamigera avellanea* | IFM42323 |
| 5 | *Penicillium griseofulvum* | IFM54313 |
| 6 | *Penicillium citirinum* | IFM54314 |
| 7 | *Neosartorya ficheri* | IFM46945 |
| 8 | *Neosartorya spinosa* | IFM46967 |
| 9 | *Neosartorya glabra* | IFM46949 |
| 10 | *Neosartorya hiratsukae* | IFM47036 |
| 11 | *Alterraria alternate* | IFM41348 |
| 12 | *Aureobasidium pullulans* | IFM41409 |
| 13 | *Chaetomium globosum* | IFM40869 |
| 14 | *Fusarium oxysporum* | IFM50002 |
| 15 | *Trichoderma viride* | IFM40938 |
| 16 | *Cladosporium cradosporioides* | IFM41450 |

(3) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). Specifically, several colonies were collected from each medium, and the fungus was suspended in 200 μL of a reagent supplied with the kit and dissolved by a heat treatment at 100° C. for 10 minutes. Centrifugation was performed at 14,800 rpm for 5 minutes, and the supernatant was collected. The concentration of the resultant genomic DNA solution was adjusted to 50 ng/μL. The genomic DNA solution was used as a template DNA in the following LAMP reaction.

(4) Preparation of Reaction Solution for LAMP Reaction 12.5 μL of 2× Reaction Mix (Tris-HCl (pH 8.8) 40 mM, KCl 20 mM, $MgSO_4$ 16 mM, $(NH_4)_2SO_4$ 20 mM, 0.2% Tween20, Betaine 1.6 M, dNTPs 2.8 mM: Eiken Chemical Co., Ltd.; Loopamp DNA amplification reagent kit), 1 μL of a primer consisting of an oligonucleotide represented by the nucleotide sequence set forth in SEQ ID NO: 16 (LPae2F3 primer: 5 pmol/μL), 1 μL of a primer consisting of an oligonucleotide represented by the nucleotide sequence set forth in SEQ ID NO: 17 (LPae2B3 primer: 5 pmol/μL), 1 μL of a primer consisting of an oligonucleotide represented by the nucleotide sequence set forth in SEQ ID NO: 18 (LPae2FIP primer: 40 pmol/μL), 1 μL of a primer consisting of an oligonucleotide represented by the nucleotide sequence set forth in SEQ ID NO: 19 (LPae2BIP primer: 40 pmol/μL), 1 μL of a primer consisting of an oligonucleotide represented by the nucleotide sequence set forth in SEQ ID NO: (LPae2LF loop primer: 20 pmol/μL), 1 μL of a primer consisting of an oligonucleotide represented by the nucleotide sequence set forth in SEQ ID NO: 21 (LPae2LB loop primer: 20 pmol/μL), 1 μL of Bot DNA Polymerase (8 U/25 μL, manufactured by Eiken Chemical Co., Ltd.) and 1 μL of the template DNA prepared above were mixed, and distilled water was added thereto, to thereby prepare a total of 25 μL of a reaction solution.

(5) LAMP Reaction

The reaction solution prepared above was subjected to a DNA amplification reaction at 63±2° C. for 60 minutes using a real-time turbidity measuring apparatus Loopamp RT-160C (manufactured by Eiken Chemical Co., Ltd.). Simultaneously, the turbidity of the reaction solution was measured (wavelength: 400 nm).

(6) Confirmation of DNA Amplification

Figure 6:
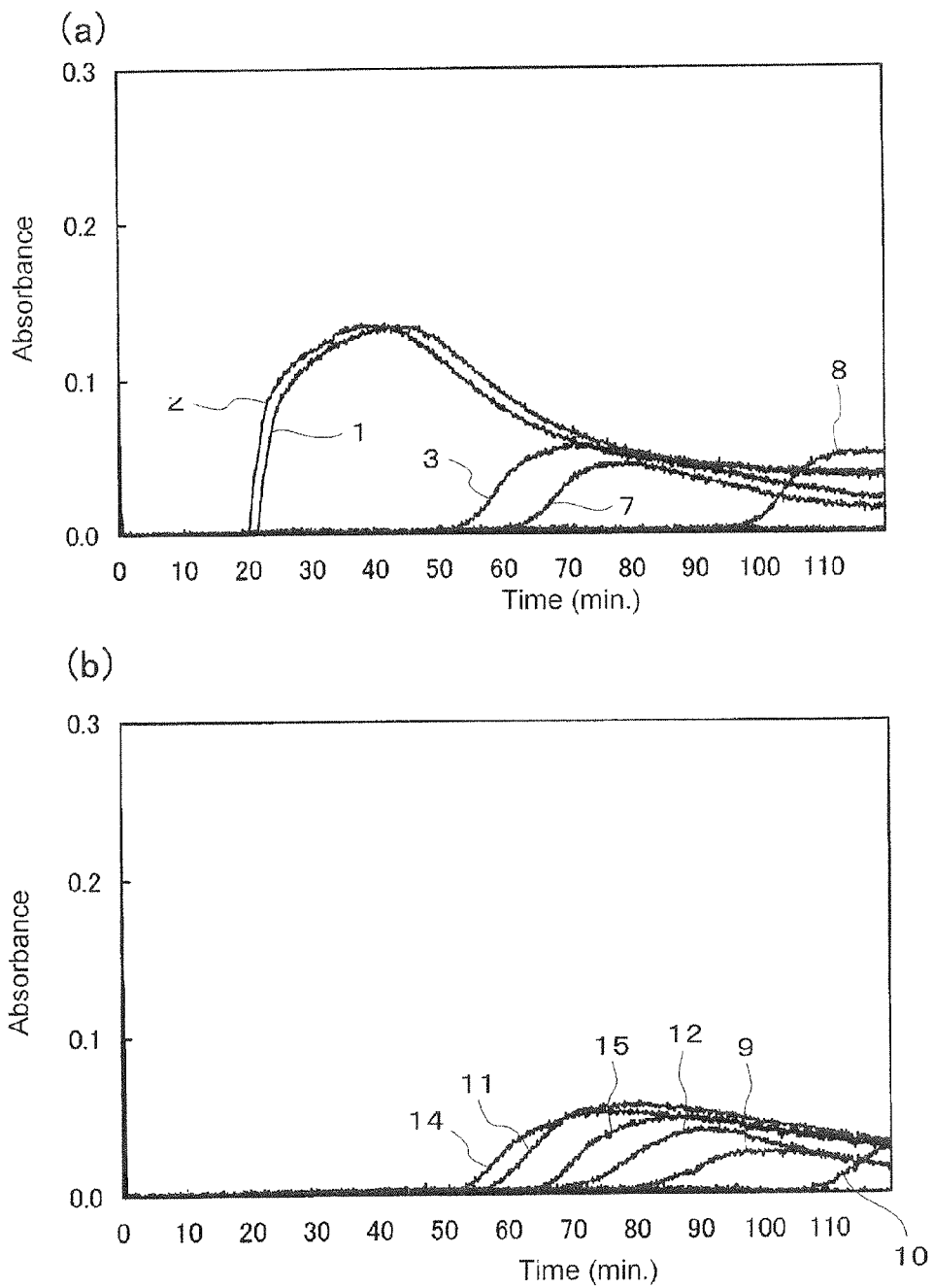
[FIG. 6] FIG. 6(*a*) and FIG. 6(*b*) each area graph illustrating the detection sensitivity of *Paecilomyces variotii* by real-time turbidity monitoring method in Example 3.

Amplification of DNA was judged to be present or not by whether or not the turbidity increased in the reaction solution. The measurement results of the turbidity of the reaction solutions are shown in FIG. 6.

As a result, the turbidity increases, that is, the DNA synthesis and amplification reactions were observed from about 20 minutes after the initiation of the reaction only in the systems where the genomic DNAs of *Paecilomyces variotii* were used as templates.

On the other hand, in the systems where the genomic DNAs of other fungi were used, the turbidity increases in the reaction solutions were not observed for 50 minutes after the initiation of the reaction. Note that, also in the systems where the genomic DNAs of fungi other than *Paecilomyces variotii* were used, the turbidity increases of the reaction solutions were observed from about 60 minutes after the initiation of the reaction. However, the phenomena are probably caused by time-dependent occurrence of a nonspecific reaction among primers or by a reaction of a small amount of primers to sites other than the target due to a long reaction time.

Example 4

Detection of *Paecilomyces variotii* by PCR Method (1) Preparation of Primers

From the nucleotide sequence regions which were specified in Example 1 above and specific to *Paecilomyces variotii*

(SEQ ID NOS: 1 to 4 and 22 to 33), partial regions which satisfy the following four conditions were searched:
1) the partial region includes several nucleotides specific to the species;
2) the partial region has a GC content of about 30% to 80%;
3) the partial region has low possibility to cause self-annealing; and
4) the partial region has a Tm value of about 55 to 65° C.

Based on the nucleotide sequences, five primer pairs including primers which consist of each of the oligonucleotides represented by the nucleotide sequences set forth in SEQ ID NOS: 7 to 9 were designed. Then, the primers were synthesized by Sigma-Aldrich Japan (desalted products, 0.02 μmol scale) and purchased.

(2) Preparation of Samples

The fungi shown in Table 5 were used as fungi to be used for evaluation of the effectiveness of the designed primers, i.e., *Paecilomyces variotii* and other heat-resistant fungi. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 30° C. for 7 days.

TABLE 5

| No. | Strain | scientific name |
| --- | --- | --- |
| 1 | NBRC4855 | *Pae. variotii* |
| 2 | NBRC7563 | *Pae. variotii* |
| 3 | NBRC5479 | *Pae. variotii* |
| 4 | NBRC31685 | *Pae. variotii* |
| 5 | IFM48421 | *B. fluva* |
| 6 | IFM51213 | *B. fluva* |
| 7 | IFM51244 | *B. nivea* |
| 8 | IFM51245 | *B. nivea* |
| 9 | IFM42323 | *H. avellanea* |
| 10 | IFM52241 | *H. avellanea* |
| 11 | IFM42243 | *T. flavus* |
| 12 | IFM53242 | *T. luteus* |
| 13 | IFM42247 | *T. trachysperumus* |
| 14 | IFM52255 | *T. wortmannii* |
| 15 | IFM53622(T) | *T. ebumeus* |

(3) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/μL.

(4) PCR Reaction

One μL of the genomic DNA solution prepared above as a DNA template, 15 μL of Pre Mix Taq (trade name, manufactured by TAKARA BIO INC.) and 11 μL of sterile distilled water were mixed, and 1 μL of a primer consisting of an oligonucleotide represented by the nucleotide sequence set forth in SEQ ID NO: 7 (Pae4F primer, 20 pmol/μL), 1 μL of a primer consisting of an oligonucleotide represented by the nucleotide sequence set forth in SEQ ID NO: 8 (Pae4R-1 primer, 20 pmol/μL) and 1 μL of a primer consisting of an oligonucleotide represented by the nucleotide sequence set forth in SEQ ID NO: 9 (Pae1R-2 primer, 20 pmol/μL) were added thereto, to thereby prepare 30 μL of a PCR reaction solution. PCR reaction solutions for the other four primer pairs were prepared in the similar manner described above.

The PCR reaction solution was subjected to a gene amplification treatment using an automatic gene amplification device thermal cycler DICE (TAKARA BIO INC.). PCR reaction conditions were 35 cycles of (i) a thermal denaturation reaction at 95° C. for 1 minute, (ii) an annealing reaction at 59° C. for 1 minute, and (iii) an elongation reaction at 72° C. for 1 minute.

(5) Confirmation of Amplified Gene Fragment

Figure 7:
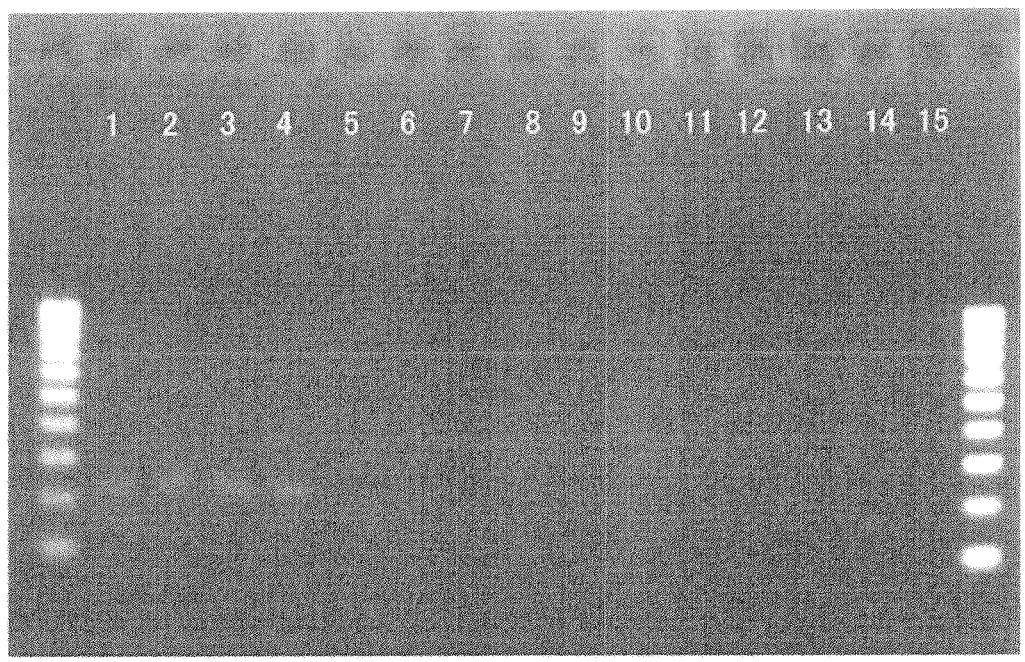
[FIG. 7]

After the PCR reaction, 2.5 μL of a sample was collected from the PCR reaction solution and electrophoresed using a 2% agarose gel, and DNA was stained with SYBR Safe DNA gel stain in 1×TAE (Invitrogen), followed by fluorescence detection under ultraviolet light, to thereby confirm whether the amplified DNA fragment was present or not. As a result, in the case of using the primer pair consisting of the oligonucleotides represented by the nucleotide sequences set forth in SEQ ID NOS: 7 to 9 of the designed five primer sets, in a sample containing genomic DNA of *Paecilomyces variotii*, amplification of gene fragments was confirmed at a position corresponding to the size expected from the designed primer pairs. On the other hand, in a sample containing no genomic DNA of *Paecilomyces variotii*, amplification of gene fragments was not confirmed. FIG. 7 shows an electrophoretogram in the agarose gel in the case of using the primer set including the oligonucleotides represented by the nucleotide sequences set forth in SEQ ID NOS: 7 to 9. The numbers in the electrophoretograms represent samples which were subjected to reactions using DNAs extracted from samples of the corresponding sample numbers in Table 5.

As a result, in the case of the samples containing the genomic DNA of *Paecilomyces variotii*, amplification of gene fragments of about 200 bp was confirmed. On the other hand, in the case of the samples containing no genomic DNA of *Paecilomyces variotii*, amplification of gene fragments was not confirmed.

The above-described results reveal that *Paecilomyces variotii* can be specifically detected by using the oligonucleotides of the present invention. Moreover, the results reveal that it is possible to easily design oligonucleotides for detecting *Paecilomyces variotii*, which can act as nucleic acid probes or nucleic acid primers for specifically detecting *Paecilomyces variotii*, based on the nucleotide sequence of the variable region of the β-tubulin gene of the present invention.

As is clear from the results of Examples 1 to 4, according to the method of the present invention, it is possible to detect *Paecilomyces variotii* easily, rapidly, and specifically.

Industrial Applicability

According to the method of detecting *Paecilomyces variotii* of the present invention, it is possible to provide a method with which *Paecilomyces variotii* can be detected specifically, easily, and rapidly. Therefore, the method of detecting *Paecilomyces variotii* of the present invention is useful for detection of *Paecilomyces variotii*, which is known to be a harmful fungus in the food industry, the toiletry industry, and the like.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A method of detecting whether *Paecilomyces variotii* is present in a sample, said method comprising
   (I) adding, to said sample, or adding to DNA prepared from DNA or RNA obtained from said sample, a primer pair or primer group selected from the group consisting of:
   (i) a primer pair in which the nucleotide sequence of one primer is the nucleotide sequence of SEQ ID NO: 5 and the nucleotide sequence of the other primer is the nucleotide sequence of SEQ ID NO: 6;
   (ii) a primer pair in which the nucleotide sequence of one primer is the nucleotide sequence of SEQ ID NO: 7 and the nucleotide sequence of the other primer is the nucleotide sequence of SEQ ID NO: 8;
   (iii) a primer pair in which the nucleotide sequence of one primer is the nucleotide sequence of SEQ ID NO: 7 and the nucleotide sequence of the other primer is the nucleotide sequence of SEQ ID NO: 9; and
   (iv) a primer group of three primers in which the nucleotide sequence of one primer is the nucleotide sequence of SEQ ID NO: 7, the nucleotide sequence of one primer is the nucleotide sequence of SEQ ID NO: 8, and the nucleotide sequence of one primer is the nucleotide sequence of SEQ ID NO: 9;
   under conditions in which the primers in said primer pair or primer group hybridize to *Paecilomyces variotii* nucleic acid if said *Paecilomyces variotii* nucleic acid is present,
   (II) performing an amplification reaction that amplifies, if present, the *Paecilomyces variotii* nucleic acid of part (I), to which said primers in said primer pair or said primer group are hybridized; and
   (III) detecting whether *Paecilomyces variotii* nucleic acid was amplified in part (II), wherein detecting *Paecilomyces variotii* nucleic acid that was amplified in part (II) is as an indication of the presence of *Paecilomyces variotii* in said sample.

2. The method of claim 1, wherein the primer pair or primer group is that of part (I)(i), a primer pair in which the nucleotide sequence of one primer is the nucleotide sequence of SEQ ID NO: 5 and the nucleotide sequence of the other primer is the nucleotide sequence of SEQ ID NO: 6.

3. The method of claim 1, wherein the amplification reaction of part (II) is performed by a polymerase chain reaction (PCR) method.

4. The method of claim 3, wherein the polymerase chain reaction (PCR) method is performed using the primer pair of part (I)(i), a primer pair in which the nucleotide sequence of one primer is the nucleotide sequence of SEQ ID NO: 5 and the nucleotide sequence of the other primer is the nucleotide sequence of SEQ ID NO: 6.

5. The method of claim 3, which further comprises electrophoresing or sequencing a product or products of the PCR.

6. The method of claim 3, wherein the PCR method integrates a nucleotide labeled with a radioactive substance or a fluorescent substance into a product or products of the PCR.

7. The method of claim 1, wherein said primer pair or said primer group is added to said sample.

8. The method of claim 1, wherein said primer pair or said primer group is added to DNA prepared from DNA or RNA obtained from said sample.

9. The method of claim 1, wherein the primer pair or primer group is that of part (I)(ii), (I)(iii) or (I)(iv).

10. The method of claim 9, wherein the primer pair or primer group is that of part (I)(ii).

11. The method of claim 9, wherein the primer pair or primer group is that of part (I)(iii).

12. The method of claim 9, wherein the primer pair or primer group is that of part (I)(iv).

* * * * *

SEQUENCE LISTING

<160> NUMBER OF SEQ ID NOS: 35

<210> SEQ ID NO 1
<211> LENGTH: 513
<212> TYPE: DNA
<213> ORGANISM: Paecilomyces variotii
<220> FEATURE:
<223> OTHER INFORMATION: strain IMF40913

<400> SEQUENCE: 1

```
tggtaaccaa atcggtgctg ctttctggta tgttgtcaac cagcaggaga aatgaaacaa      60
agagcctaga gtccgtttgg ggacgtggaa ggctcaagtg atcagaattg gaggtgctaa     120
cgatcctata ggcagaccat ctctggtgag cacggccttg acggctctgg tgtgtaagta     180
cacgatatct ggggatgctt cgacacgaaa tcgagagaga cgactgacga tggattagct     240
acaatggctc ctccgacctt cagctcgagc gcatgaacgt ctacttcaac gaggtagttg     300
ttgaccctat gatcccaaga ggaacgctcc atgagctcac caataaatag gccgctggca     360
agaagtacgt tcctcgtgcc gtcctcgtcg acctcgagcc tggtaccatg gacgctgtcc     420
gtgctggtcc tttcggccag ctcttccgcc ctgacaactt cgtcttcggt cagtccggtg     480
ctggtaacaa ctgggccaag ggtcactaca ctg                                  513
```

<210> SEQ ID NO 2
<211> LENGTH: 515
<212> TYPE: DNA
<213> ORGANISM: Paecilomyces variotii
<220> FEATURE:
<223> OTHER INFORMATION: strain IMF40915
<220> FEATURE:
<221> NAME/KEY: misc_feature
<222> LOCATION: (258)..(258)
<223> OTHER INFORMATION: n is a, c, g, or t

<400> SEQUENCE: 2

```
tggtaaccaa atcggtgctg ctttctggta tgttgtcaac cagcaggaga aatgaaacaa      60
agagcctgga gtccgtttgg ggacgtcgaa ggctcaagtg atgagacttg gaggtgctaa     120
cgaccctata ggcagaccat ctctggtgag cacggccttg acggctccgg tgtgtaagta     180
cacgatatct ggggatgctt cgacacgaaa tcgagagaga cgactgacga tggattagct     240
acaatggctc ctccgacnac cttcagctcg agcgcatgaa tgtctacttc aacgaggtag     300
ttgttgaccc tatgatccca agaggaacgc cccatgagct caccaataaa taggccgctg     360
gcaagaagta cgttcctcgt gccgtcctcg tcgacctcga gcctggtacc atggacgctg     420
tccgtgctgg tcctttcggc cagctcttcc gccctgacaa cttcgtcttc ggtcagtccg     480
gtgctggtaa caactgggcc aaggtcacta cactg                                515
```

<210> SEQ ID NO 3
<211> LENGTH: 518
<212> TYPE: DNA
<213> ORGANISM: Paecilomyces variotii
<220> FEATURE:
<223> OTHER INFORMATION: strain EU037073

<400> SEQUENCE: 3

```
ggtaaccaaa tcggtgctgc tttctggtat gttggaaatc aataggagaa atgaaagaaa      60
gagcccgggt gtcatattga gacgtggaag gctcaggtta tgaagattga gggtgctaac     120
tatgctatag gcagaccatc tctggcgagc acggcattga cggctctggt gtgtgagtac     180
acacgatatc tggagacgct tggacatcga atcgacgggt gactgacgat ggattagcta     240
```

```
caatggcacc tccgacctcc agctcgagcg catgaacgtc tacttcaacg aggtagttgt    300 tggcccctatg ataccgataa ggacgctcca tatgctcacc aatactttag gctgctggca    360
agaagtatgt tcctcgtgcc gtcctcgtcg accttgagcc tggtaccatg gacgctgtcc    420
cgtgccggtc ctttcggcca gctcttccgc cctgacaact tcgtcttcgg tcagtcccgg    480
tgcggtaaca actgggccaa gggtcactac actgaggg                            518

<210> SEQ ID NO 4
<211> LENGTH: 519
<212> TYPE: DNA
<213> ORGANISM: Paecilomyces variotii
<220> FEATURE:
<223> OTHER INFORMATION: strain IFM50293

<400> SEQUENCE: 4
tggtaaccaa atcggtgctg ctttctggta tgttgaccag caggagaaat gaaacaacga     60
gcctggggtc catttgggga cgtggaaggc tcagatgatg agaattggag gtgctaacga    120
tcctacaggc agaccatctc tggcgagcac ggccttgacg gctctggtgt gtaagtacac    180
acgatatctc gaggcgtttc gacgtggaat cgagagagat gactgacgat gaattagcta    240
caatggctcc tccgaccttc agctcgagcg catgaacgtc tacttcaacg aggtagttgt    300 tgacccctatg atcccaaaag gaacgcccca tgagctcacc aataaatagg ccgctggcaa    360
gaagtacgtc cctcgtgccg tcctcgtcga cctcgagcct ggtaccatgg acgctgtccg    420
tgccggtcct ttcggccagc tcttccgccc tgacaacttc gtcttcggtc agtccggtgc    480
tggtaacaac tgggccaagg gtcactacac tgagggtag                           519

<210> SEQ ID NO 5
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 5
cctagagtcc gtttggggac                                                 20

<210> SEQ ID NO 6
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 6
gttcctcttg ggatcatagg                                                 20

<210> SEQ ID NO 7
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 7
gagcacggcc ttgacggct                                                  19

<210> SEQ ID NO 8
<211> LENGTH: 20
<212> TYPE: DNA
```

```
<213> ORGANISM: Artificial
<220> FEATURE:
<223> OTHER INFORMATION: Artificially synthesized primer sequence

<400> SEQUENCE: 8
gcatatggag cgtccttatc                                                    20

<210> SEQ ID NO 9
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 9
gctcatgggg cgttcctctt                                                    20

<210> SEQ ID NO 10
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 10
acgatcctat aggcagacca                                                    20

<210> SEQ ID NO 11
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 11
ccagcggcct atttattggt                                                    20

<210> SEQ ID NO 12
<211> LENGTH: 40
<212> TYPE: DNA
<213> ORGANISM: Artificial
<220> FEATURE:
<223> OTHER INFORMATION: Artificially synthesized primer sequence

<400> SEQUENCE: 12
cgtctctctc gattccgtgt cgccttgacg gctctggtgt                               40

<210> SEQ ID NO 13
<211> LENGTH: 39
<212> TYPE: DNA
<213> ORGANISM: Artificial
<220> FEATURE:
<223> OTHER INFORMATION: Artificially synthesized primer sequence

<400> SEQUENCE: 13
ctccgacctt cagctcgagc ggagcgttcc tcttgggat                                39

<210> SEQ ID NO 14
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 14
tccccagata tcgtgtactt ac                                                 22
```

```
<210> SEQ ID NO 15
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 15
acttcaacga ggtagttgtt g                                              21

<210> SEQ ID NO 16
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 16
cgatatctgg ggatgcttcg                                                20

<210> SEQ ID NO 17
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 17
cgtccatggt accaggct                                                  18

<210> SEQ ID NO 18
<211> LENGTH: 42
<212> TYPE: DNA
<213> ORGANISM: Artificial
<220> FEATURE:
<223> OTHER INFORMATION: Artificially synthesized primer sequence

<400> SEQUENCE: 18
atgcgctcga gctgaaggtc cggaatcgag agagagacga ct                       42

<210> SEQ ID NO 19
<211> LENGTH: 42
<212> TYPE: DNA
<213> ORGANISM: Artificial
<220> FEATURE:
<223> OTHER INFORMATION: Artificially synthesized primer sequence

<400> SEQUENCE: 19
tgatcccaag aggaacgccc cacgaggaac gtacttcttg cc                       42

<210> SEQ ID NO 20
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 20
ggaggagcca ttgtagctaa                                                20

<210> SEQ ID NO 21
<211> LENGTH: 21
<212> TYPE: DNA
<213> ORGANISM: Artificial
<220> FEATURE:
```

<223> OTHER INFORMATION: Artificially synthesized primer sequence

<400> SEQUENCE: 21
gagctcacca ataaataggc c                                               21

<210> SEQ ID NO 22
<211> LENGTH: 470
<212> TYPE: DNA
<213> ORGANISM: Paecilomyces variotii
<220> FEATURE:
<223> OTHER INFORMATION: strain NBRC4855

<400> SEQUENCE: 22
gatgaaagaa agagcccggg tgtcatattg agacgtggaa ggctcaggtt atgaagattg     60
agggtgctaa ctatgctata ggcagaccat ctctggcgag cacggccttg acggctctgg    120
tgtgtgagta cacacgatat ctggagacgc ttggacatcg aatcgacggg tgactgacga    180
tggattagct acaatggcac ctccgacctc cagctcgagc gcatgaacgt ctacttcaac    240
gaggtagttg ttggccctat gataccgata aggacgctcc atatgctcac caatacttta    300
ggctgctggc aagaagtatg ttcctcgtgc cgtcctcgtc gaccttgagc ctggtaccat    360
ggacgctgtc cgtgccggtc ctttcggcca gctcttccgc cctgacaact tcgtcttcgg    420
tcagtccggt gctggtaaca actgggccaa gggtcactac actgagggta              470

<210> SEQ ID NO 23
<211> LENGTH: 506
<212> TYPE: DNA
<213> ORGANISM: Paecilomyces variotii
<220> FEATURE:
<223> OTHER INFORMATION: strain IFM52147

<400> SEQUENCE: 23
aaatcggtgc tgctttctgg tatgttcgaa atcaatagga gaaatgaaag aaagagcccg    60
ggtgtcattc tgagacgtgg aaggctcagg ttatgaagat tgagggtgct aactatgcta    120
taggcagacc atctctggcg agcacggcct tgacggctct ggtgtgtgag tacacacgat    180
atctggagac gcttggacat cgaatcaacg ggtgactgac gatggattag ctacaatggc    240
acctccgacc tccagctcga gcgcatgaac gtctacttca atgaggtagt tgttggccct    300
atgataccga taaggacgct ccatatgctc accaatactt taggctgctg gcaagaagta    360
tgttcctcgt gccgtactcg tcgaccttga gcccggtacc atggacgctg tccgtgccgg    420 tccttcggc cagctcttcc gccctgacaa cttcgtcttc ggtcagtccg gtgctggtaa    480
caactgggcc aagggtcact acactg                                         506

<210> SEQ ID NO 24
<211> LENGTH: 518
<212> TYPE: DNA
<213> ORGANISM: Paecilomyces variotii
<220> FEATURE:
<223> OTHER INFORMATION: strain IFM52145

<400> SEQUENCE: 24
tggtaaacca atcggtgct gctttctggt atgttggaaa tcaataggag aaatgaaaga    60
aagagcccgg gtgtctgttt gagacgtgga aggctcaggt tatgaagatt gagggtgcta    120
attatgctat aggcagacca tctctggcga gcacggcctt gacggttctg tgtgtgagt    180 acacgatatc tggagacgct tggacatcga atcgacggt gactgacgat ggattagcta    240
caatggcacc tccgacctcc agctcgagcg catgaacgtc tacttcaacg aggtagttgt    300

```
tggccctatg ataccgataa ggacgctcca tatgctcacc aatactttag gctgctggca    360
agaagtatgt tcctcgtgcc gtcctcgtcg accttgagcc tggtaccatg gacgctgtcc    420
gtgccggtcc tttcggccag ctcttccgcc ctgacaactt cgtcttcggt cagtccggtg    480
ctggtaacaa ctgggccaag ggtcactaca ctgagggt                            518
```

<210> SEQ ID NO 25  
<211> LENGTH: 461  
<212> TYPE: DNA  
<213> ORGANISM: Paecilomyces variotii  
<220> FEATURE:  
<223> OTHER INFORMATION: strain IFM51028

<400> SEQUENCE: 25

```
aaatgaaaga aagagcccgg gtgtctgttt gagacgtgga aggctcaggt tatgaagatt     60
gagggtgcta actatgctat aggcagacca tctctggcga gcacggtctt gacggctctg    120
gtgtgtgagt acacacgata tctggagacg cttggacatc gaatcgacgg gtgactgacg    180
atggattagc tacaatggca cctccgacct ccagctcgag cgcatgaacg tctacttcaa    240
cgaggtagtt gttggcccta tgatactgat aaggacgctc catatgctca ccaaacttt     300 aggctgctgg caagaagtat gttcctcgtg ccgtcctcgt cgaccttgag cctggtacca    360
tggacgctgt ccgtgccggt cctttcggcc agctcttccg ccctgacaac ttcgtcttcg    420
gtcagtccgg tgctggtaac aactgggcca aggtcacta c                         461
```

<210> SEQ ID NO 26  
<211> LENGTH: 522  
<212> TYPE: DNA  
<213> ORGANISM: Paecilomyces variotii  
<220> FEATURE:  
<223> OTHER INFORMATION: strain IFM51195

<400> SEQUENCE: 26

```
gtggtaacca aatcggtgct gctttctggt atgttggaaa tcaataggag aaatgaaaga     60
aggagcccgg gtgtctgttt gaggcgtgga aggctcaggt tatgaagatt gagggtgcta    120
actatgctat aggcagacca tctctggcga gcacggtctt gacggctctg gtgtgtgagt    180
acacacgata tctggagacg cttggacatc gaatcgacgg gtgactgacg atggattagc    240
tacaatggca cctccgacct ccagctcgag cgcatgaacg tctacttcaa cgaggtagtt    300
gttggcccta tgataccgat aaggacgctc catatgctca ccgataaatt aggctgctgg    360
caagaagtat gttccacgtg ccgtcctcgt cgaccttgag cctggtacca tggacgctgt    420
ccgtgccggt cctttcggcc agctcttccg ccctgacaac ttcgtcttcg gtcagtccgg    480
tgctggtaac aactgggcca aggtcacta cactgagggt ag                        522
```

<210> SEQ ID NO 27  
<211> LENGTH: 523  
<212> TYPE: DNA  
<213> ORGANISM: Paecilomyces variotii  
<220> FEATURE:  
<223> OTHER INFORMATION: strain IFM55619

<400> SEQUENCE: 27

```
agtggtaacc aaatcggtgc tgctttctgg tatgttggaa atcaagagga gaaatgaaag     60
aaagagcccg ggtgtctgtt tgagacgtgg aaggctcagg ttatgaagat tgagggtgct    120
aactatgcta taggcagacc atctctggcg agcacggtct tgacggctct ggtgtgtgag    180
```

```
tacacacgat atctggagac gcttggacat cgaatcgacg ggtgactgac gatggattag    240
ctacaatggc acctccgacc tccagctcga gcgcatgaac gtctacttca acgaggtagt    300
tgttggccct atgatactga taaggacgct ccatatgctc accaacactt taggctgctg    360
gcaagaagta tgttcctcgt gccgtcctcg tcgaccttga gctggtacc atggacgctg     420 tccgtgccgg tcctttcggc cagctcttcc gccctgacaa cttcgtcttc ggtcagtccg    480
gtgctggtaa caactgggcc aagggtcact acactgaggg tag                      523
```

<210> SEQ ID NO 28
<211> LENGTH: 463
<212> TYPE: DNA
<213> ORGANISM: Paecilomyces variotii
<220> FEATURE:
<223> OTHER INFORMATION: strain NBRC5479

<400> SEQUENCE: 28

```
acaacgagcc tggggtccat ttgagggcgt ggaaggctca gatgatgaga attgaaggtg     60
ctaacgatcc tacaggcaga ccatctctgg cgagcacggc cttgacggct ctggtgtgta    120
agtacacacg atatctcaga gcacttcgac gcggaatcga gagagaactg acgatggatt   180
agctacaatg gctcttccga ccttcagctc gagcgcatga acgtctactt caacgaggta    240
gttgttgacc ctatgatccc aagaggaacg ccccatgagc tcaccaataa ataggccgct   300
ggcaagaagt acgttcctcg tgccgtcctc gtcgaccttg agcctggtac catggacgct   360
gtccgcgccg gtcctttcgg ccagctcttc cgccctgaca acttcgtctt cggtcagtcc    420
ggtgctggta caactgggc caagggtcac tacactgagg gta                       463
```

<210> SEQ ID NO 29
<211> LENGTH: 518
<212> TYPE: DNA
<213> ORGANISM: Paecilomyces variotii
<220> FEATURE:
<223> OTHER INFORMATION: strain IFM51027

<400> SEQUENCE: 29

```
ggtaaccaaa tcggtgctgc tttctggtat gttgacaacc agctggagaa atggaacaac     60
gagcctgggg tccatttgag ggtgtggaag gctcagatga tgagaattga aggtgctaac    120
gatcctacag gcagaccatc tctggcgagc acggccttga cggctctggt gtgtaagtac    180
acccgatatc tcagagcact tcgacgcgga atcgagagag aactgacgat ggattagcta    240
caatggctcc tccgatcttc agctcgagcg catgaacgtc tacttcaacg aggtagttgt    300
tgaccctatg atcccaagag gaacgcccca tgagctcacc aataaatagg ccgctggcaa    360
gaagtacgtt cctcgtgccg tcctcgtcga ccttgagcct ggtaccatgg acgctgtccg    420
tgccggtcct ttcggccagc tcttccgccc tgacaacttc gtcttcggtc agtccggtgc    480
tggtaacaac tgggccaagg gtcactacac tgagggta                             518
```

<210> SEQ ID NO 30
<211> LENGTH: 450
<212> TYPE: DNA
<213> ORGANISM: Paecilomyces variotii
<220> FEATURE:
<223> OTHER INFORMATION: strain NBRC31967

<400> SEQUENCE: 30

```
aaacaaagag cctggagttc atttggctcg agtgatcaga attggagggt gctaacgacc     60
ctataggcag accatctctg gtgagcacgg ccttgacggc tctggtgtgt aagtacacga    120
```

```
tatctgggga tgcttcgaca cggaatcgag acgactgacg atggattagc tacaatggct      180
cctccgacct tcagctcgag cgcatgaacg tctacttcaa cgaggtagtt gttggcccta      240
taatcccaag aggaacgccc catgagctca ccaataaata ggccgctggc aagaagtacg      300
ttcctcgtgc cgtcctcgtc gacctcgagc ctggtaccat ggacgctgtc cgtgctggtc      360
ctttcggcca gctcttccgc cctgacaact tcgtcttcgg tcagtccggt gctggtaaca      420
actgggccaa gggtcactac actgaagggt                                       450

<210> SEQ ID NO 31
<211> LENGTH: 497
<212> TYPE: DNA
<213> ORGANISM: Paecilomyces variotii
<220> FEATURE:
<223> OTHER INFORMATION: strain NBRC31685
<220> FEATURE:
<221> NAME/KEY: misc_feature
<222> LOCATION: (7)..(7)
<223> OTHER INFORMATION: n is a, c, g, or t

<400> SEQUENCE: 31
tggtaancaa atcggtgctg ctttctggta tgttgtcaac cagcaggaga aatgaaacaa       60
agagcctgga gttcatttgg ctcgagtgat cagaattgga ggtgctaacg accctatagg      120
cagaccatct ctggtgagca cggccttgac ggctctggtg tgtaagtaca cgatatctgg      180
ggatgcttcg acacggaatc gagacgactg acgatggatt agctacaatg gctcctccga      240
ccttcagctc gagcgcatga acgtctactt caacgaggta gttgttggcc ctataatccc      300
aagaggaacg ccccatgagc tcaccaataa ataggccgct ggcaagaagt acgttcctcg      360
tgccgtcctc gtcgacctcg agcctggtac catggacgct gtccgtgctg gtcctttcgg      420
ccagctcttc gccctgaca acttcgtctt cggtcagtcc ggtgctggta acaactgggc       480
caagggtcac tacactg                                                     497

<210> SEQ ID NO 32
<211> LENGTH: 519
<212> TYPE: DNA
<213> ORGANISM: Paecilomyces variotii
<220> FEATURE:
<223> OTHER INFORMATION: strain SUM3339
<220> FEATURE:
<221> NAME/KEY: misc_feature
<222> LOCATION: (1)..(1)
<223> OTHER INFORMATION: n is a, c, g, or t

<400> SEQUENCE: 32
ntggtaacca aatcggtgct gctttctggt atgttgtcaa ccagcaggag aaatgaaaca       60
aagagcctgg agtccgtttg ggacgtcgaa ggctcaagt gatgagaatt ggaggtgcta      120
acgaccctat aggcagacca tctctggtga gcacggcctt gacggctctg gtgtgtaagt      180
acacgatatc tggggatgct tcgacacgga atcgagagag acgactgacg atggattagc      240
tacaatggct cctccgacct tcagctcgag cgcatgaacg tctacttcaa cgaggtagtt      300
gttggcccta taatcccaag aggaacgccc catgagctca ccaataaata ggccgctggc      360
aagaagtacg ttcctcgtgc cgtcctcgtc gacctcgagc ctggtaccat ggacgctgtc      420
cgtgctggtc ctttcggcca gctcttccgc cctgacaact tcgtcttcgg tcagtccggt      480
gctggtaaca actgggccaa gggtcactac actgagggt                             519

<210> SEQ ID NO 33
```

```
<211> LENGTH: 516
<212> TYPE: DNA
<213> ORGANISM: Paecilomyces variotii
<220> FEATURE:
<223> OTHER INFORMATION: strain IFM50294

<400> SEQUENCE: 33
tggtaaccaa atcggtgctg ctttctggta tgttgtcaac cagcaggaga aatgaaacaa      60
agagcctgga gtccgtttgg ggacgtcgaa ggctcaagtg atgagaattg ggggtgctaa     120
cgaccctata ggcagaccat ctctggtgag cacggccttg acggctctgg tgtgtaagta     180
cacgatatct ggggatgctt cgacacggaa tcgagacgac tgacgatgga ttagctacaa     240
tggctcctcc gaccttcagc tcgagcgcat gaacgtctac ttcaacgagg tagttgttgg     300
ccctataatc ccaagaggaa cgccccatga gctcaccaat aaataggccg ctggcaagaa     360
gtacgttcct cgtgccgtcc tcgtcgacct cgagcctggt accatggacg ctgtccgtgc     420
tggtcctttc ggccagctct tccgccctga caacttcgtc ttcggtcagt ccggtgctgg     480
taacaactgg gccaagggtc actacactga gggtag                               516

<210> SEQ ID NO 34
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 34
ggtaaccaaa tcggtgctgc tttc                                             24

<210> SEQ ID NO 35
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 35
accctcagtg tagtgaccct tggc                                             24
```